(12) United States Patent
Altbach et al.

(10) Patent No.: US 10,782,373 B2
(45) Date of Patent: *Sep. 22, 2020

(54) SYSTEM AND METHOD FOR IMAGE PROCESSING WITH HIGHLY UNDERSAMPLED IMAGING DATA

(71) Applicant: Arizona Board of Regents on Behalf of the University of Arizona, Tucson, AZ (US)

(72) Inventors: Maria Altbach, Tucson, AZ (US); Ali Bilgin, Tucson, AZ (US); Chuan Huang, Stony Brook, NY (US); Christian Graff, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/530,905

(22) Filed: Aug. 2, 2019

(65) Prior Publication Data

US 2019/0353733 A1 Nov. 21, 2019

Related U.S. Application Data

(63) Continuation of application No. 14/371,995, filed as application No. PCT/US2013/024500 on Feb. 1, 2013, now Pat. No. 10,393,839.

(Continued)

(51) Int. Cl.
| | | |
|---|---|---|
| *G01R 33/54* | (2006.01) | |
| *G01R 33/50* | (2006.01) | |
| *G16H 30/20* | (2018.01) | |
| *A61B 5/055* | (2006.01) | |
| *A61B 5/00* | (2006.01) | |

(Continued)

(52) U.S. Cl.
CPC .............. *G01R 33/54* (2013.01); *A61B 5/055* (2013.01); *A61B 5/4244* (2013.01); *G01R 33/4818* (2013.01); *G01R 33/50* (2013.01); *G01R 33/5611* (2013.01); *G06F 19/321* (2013.01); *G16H 30/20* (2018.01); *G01R 33/5617* (2013.01); *G06T 2211/436* (2013.01)

(58) Field of Classification Search
CPC ..................................................... G01R 33/54
USPC ......................................................... 702/189
See application file for complete search history.

(56) References Cited

U.S. PATENT DOCUMENTS

| | | | | |
|---|---|---|---|---|
| 8,310,233 B2* | 11/2012 | Trzasko | ............... | G01R 33/561 324/307 |
| 8,384,383 B2* | 2/2013 | Frahm | ................ | G01R 33/4824 324/307 |

(Continued)

*Primary Examiner* — Ricky Ngon
(74) *Attorney, Agent, or Firm* — Davis Wright Tremaine LLP; Michael J. Donohue

(57) ABSTRACT

A system and method for processing highly undersampled multi-echo spin-echo data by linearizing the slice-resolved extended phase graph model generates highly accurate $T_2$ maps with indirect echo compensation. Principal components are used to linearize the signal model to estimate the $T_2$ decay curves which can be fitted to the slice-resolved model for T2 estimation. In another example of image processing for highly undersampled data, a joint bi-exponential fitting process can compensate for image variations within a voxel and thus provide partial voxel compensation to produce more accurate $T_2$ maps.

20 Claims, 24 Drawing Sheets

Related U.S. Application Data

(60) Provisional application No. 61/687,788, filed on May 1, 2012, provisional application No. 61/633,017, filed on Feb. 3, 2012.

(51) Int. Cl.
  *G01R 33/561* (2006.01)
  *G06F 19/00* (2018.01)
  *G01R 33/48* (2006.01)

(56) References Cited

U.S. PATENT DOCUMENTS

| | | | | |
|---|---|---|---|---|
| 8,723,518 B2* | 5/2014 | Seiberlich | ............ | G01R 33/543 |
| | | | | 324/307 |
| 9,607,392 B2* | 3/2017 | Crainiceanu | ........... | G06T 7/0012 |
| 2006/0250132 A1* | 11/2006 | Reeder | ............... | G01R 33/4828 |
| | | | | 324/307 |
| 2007/0055134 A1* | 3/2007 | Fuderer | ............... | G01R 33/5611 |
| | | | | 600/410 |
| 2008/0089581 A1* | 4/2008 | Pitie | .................... | H04N 1/4074 |
| | | | | 382/162 |
| 2011/0175610 A1* | 7/2011 | Griswold | ........... | G01R 33/4824 |
| | | | | 324/309 |
| 2011/0254549 A1* | 10/2011 | Lin | .................... | G01R 33/5611 |
| | | | | 324/309 |
| 2013/0121550 A1* | 5/2013 | Chang | .................. | G06T 11/003 |
| | | | | 382/130 |
| 2013/0343625 A1* | 12/2013 | Samsonov | ............ | G06T 11/005 |
| | | | | 382/131 |
| 2015/0302599 A1* | 10/2015 | Crainiceanu | .......... | G06T 7/0012 |
| | | | | 382/131 |

\* cited by examiner

| PERCENT ERROR OF $T_2$ ESTIMATES FOR PHANTOM DATA ACQUIRED WITH STANDARD SAMPLING | | | | | | | |
|---|---|---|---|---|---|---|---|
| | | | EXPONENTIAL FITTING | | | | |
| | VIAL | GOLD STANDARD | FA=180 | FA=160 | FA=140 | FA=120 | |
| ORIGINAL CURVES | A | 210.0 | 5.7% | 5.7% | 9.6% | 18.3% | |
| | B | 159.3 | 3.6% | 2.8% | 5.9% | 13.4% | |
| | C | 80.7 | 3.2% | 2.1% | 5.0% | 12.0% | |
| RECOVERED CURVES | A | 210.0 | 5.6% | 5.7% | 9.8% | 18.4% | |
| | B | 159.3 | 3.6% | 2.7% | 6.0% | 13.6% | |
| | C | 80.7 | 3.1% | 1.9% | 5.0% | 12.0% | |
| | | SEPG FITTING WITH $T_1 = +\infty$ | | | | | |
| ORIGINAL CURVES | A | 210.0 | 0.7% | -0.9% | -2.0% | -3.7% | |
| | B | 159.3 | -1.2% | -3.0% | -4.0% | -5.5% | |
| | C | 80.7 | -0.5% | -2.9% | -4.2% | -5.8% | |
| RECOVERED CURVES | A | 210.0 | 0.8% | -0.9% | -1.9% | -3.8% | |
| | B | 159.3 | -1.2% | -3.0% | -4.0% | -5.6% | |
| | C | 80.7 | -0.6% | -2.9% | -4.2% | -5.8% | |
| | | SEPG FITTING WITH $T_1$ OPTIMIZED (500ms) | | | | | |
| ORIGINAL CURVES | A | 210.0 | 2.4% | 1.2% | 1.8% | 3.2% | |
| | B | 159.3 | 0.0% | -1.6% | -1.6% | -0.8% | |
| | C | 80.7 | -0.4% | -2.5% | -3.2% | -3.6% | |
| RECOVERED CURVES | A | 210.0 | 2.4% | 1.2% | 1.8% | 3.1% | |
| | B | 159.3 | 0.0% | -1.6% | -1.6% | -0.9% | |
| | C | 80.7 | -0.4% | -2.5% | -3.2% | -3.6% | |

FIG.5

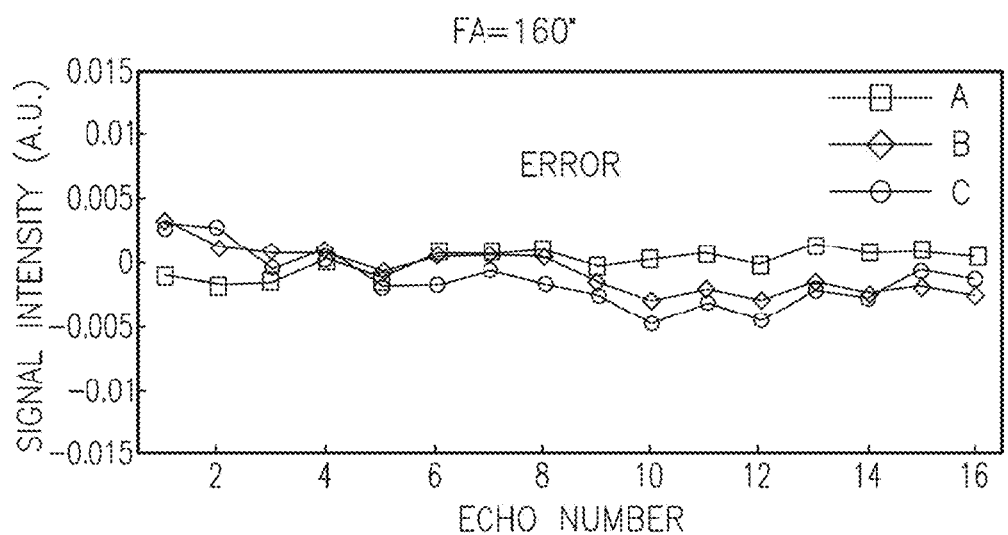
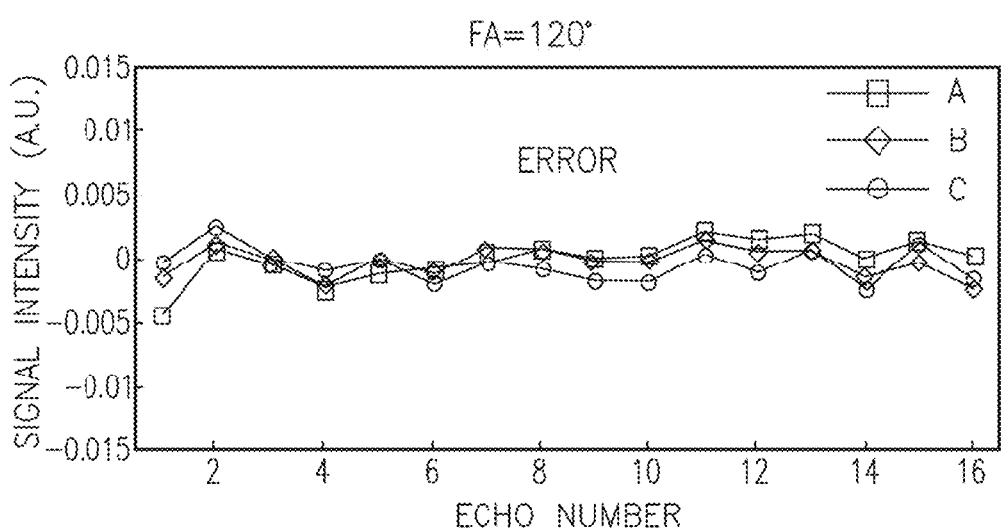
FIG.6B

PERCENT ERROR OF $T_2$ ESTIMATES FOR HIGHLY UNDERSAMPLED PHANTOM DATA

| FITTING ALGORITHM | VIAL | GOLD STANDARD | FA=180 | FA=160 | FA=140 | FA=120 |
|---|---|---|---|---|---|---|
| SEPG FITTING WITH $T_1 = +\infty$ | A | 210.0 | -0.9% | -2.1% | -3.5% | -4.0% |
| | B | 159.3 | 0.3% | -0.9% | -4.0% | -4.7% |
| | C | 80.7 | 0.5% | -0.4% | -4.6% | -4.8% |
| SEPG FITTING WITH $T_1$ OPTIMIZED (500ms) | A | 210.0 | 1.0% | -0.1% | -0.2% | -2.3% |
| | B | 159.3 | 1.6% | 0.5% | -1.8% | -0.1% |
| | C | 80.7 | 0.6% | 0.0% | -4.0% | -2.7% |

FIG. 7

| | GOLD STANDARD (ms) | FA=180° | | FA=120° | |
|---|---|---|---|---|---|
| | | CURLIE+ SEPG | REPCOM | CURLIE+ SEPG | REPCOM |
| a | 53.2 | −2.3% | 6.4% | −3.2% | 20.7% |
| b | 77.9 | 1.0% | 14.4% | 3.1% | 38.9% |
| c | 64.0 | −2.0% | 12.0% | −1.3% | 36.4% |

PERCENT ERROR OF $T_2$ ESTIMATES FOR PHANTOM DATA ACQUIRED WITH THE LIVER DATA SHOWN IN FIGURE 7

FIG.11

| TUBE INNER DIAMETER | | 6 mm | | 8 mm | | 10 mm | | 13 mm | |
|---|---|---|---|---|---|---|---|---|---|
| ROI TYPE | | TIGHT | EXPANDED | TIGHT | EXPANDED | TIGHT | EXPANDED | TIGHT | EXPANDED |
| GOLD STANDARD 92.8 ms | JBF | -2.6 | -2.6 | -1.0 | -1.0 | 0.8 | 0.9 | 2.4 | 2.5 |
| | RF | -12.0 | 3.6 | -4.2 | -2.7 | 1.4 | 3.6 | 8.6 | 6.4 |
| | VBF | 8.3 | -23.1 | 15.2 | -14.0 | 18.5 | -0.3 | 24.2 | -9.8 |
| GOLD STANDARD 176.2 ms | JBF | -5.7 | -5.3 | -4.9 | -4.9 | -3.5 | -3.1 | 2.4 | 2.5 |
| | RF | 55.7 | 78.5 | -3.7 | 19.1 | -10.3 | -6.4 | 3.5 | 3.9 |
| | VBF | 61.0 | -17.5 | 36.7 | -11.1 | 23.0 | -18.9 | 38.4 | 3.0 |

FIG.15

| GOLD STANDARD | FITTING METHOD | 6 mm | 8 mm | 10 mm | 13 mm |
|---|---|---|---|---|---|
| 179.8 | JBF | 166.0 | 164.5 | 177.4 | 183.9 |
| | SINGLE EXP. | 58.1 | 96.6 | 111.9 | 122.7 |
| 69.0 | JBF | 64.7 | 65.0 | 69.7 | 71.0 |
| | SINGLE EXP. | 49.3 | 52.5 | 55.3 | 59.0 |

FIG.16

SYSTEM AND METHOD FOR IMAGE PROCESSING WITH HIGHLY UNDERSAMPLED IMAGING DATA

RELATED APPLICATIONS

This application is a continuation of U.S. patent application Ser. No. 14/371,995, filed Jul. 11, 2014, which is a 371 Nationalization of International Patent Application No. PCT/US2013/024500, filed Feb. 1, 2013, which claims the benefit of U.S. Patent Application No. 61/687,788, filed May 1, 2012, and U.S. Patent Application No. 61/633,017, filed Feb. 3, 2012, the entire disclosures and content of which are hereby incorporated by reference in their entirety.

FEDERAL FUNDING ACKNOWLEDGEMENT

This invention was made with government support under Grant/Contract No. R01 HL085385, awarded by the National Institutes of Health. The government has certain rights in the invention.

BACKGROUND OF THE INVENTION

Field of the Invention

The present disclosure relates generally to image processing and, more specifically, to a system and method for image processing using highly undersampled imaging data.

Description of the Related Art

Spin-spin ($T_2$) relaxation is one of the main contrast mechanisms in MRI. Although most clinical applications use qualitative (visual) information derived from $T_2$-weighted images, there is an increasing interest in $T_2$ mapping (1-10).

Because single-echo spin-echo $T_2$ mapping requires long acquisition times, its translation to the clinic has been limited by its time inefficiency. In order to reduce the acquisition times it is customary to use multi-echo spin-echo (MESE) pulse sequences, where several echo time (TE) points are acquired per repetition time (TR) period by using a train of 180° refocusing pulses after the initial 90° excitation pulse. To further accelerate $T_2$ data acquisition, a fast (or turbo) spin-echo approach where several k-space lines of data are acquired per TR period is commonly used. For the sake of speed in $T_2$ mapping (while maintaining high spatial and temporal resolution), the use of TE data sets that are undersampled in k-space has been proposed in conjunction with a fast spin-echo approach. Several algorithms have been described to recover $T_2$ information from these highly reduced TE data sets (11-16). Recently, the focus has been on model-based $T_2$ mapping algorithms. Doneva et al. proposed to exploit the temporal sparsity of the exponential decay while reconstructing all TE images under the framework of compressed sensing (13, 16). Block et al. proposed a model-based algorithm for radial fast-spin-echo acquisitions to directly reconstruct $I_0$ and $R_2$ ($1/T_2$) maps from the measured k-space data (11). Because $I_0$ and $R_2$ values have very different scales the gradient-based minimization process requires a scaling factor which needs to be fine-tuned for accurate $T_2$ estimation (12). Our group has recently developed the REPCOM (REconstruction of Principal COmponent coefficient Maps) algorithm which linearizes the signal model using principal component analysis (PCA). REPCOM exploits the spatial and temporal sparsity of the TE images, and provides accurate $T_2$ estimates from highly undersampled data without the need of a scaling factor for the fitted parameters.

The algorithms described above, including REPCOM, rely on the assumption that the signal follows an exponential decay. However, in MESE acquisitions the decay is generally contaminated by indirect echoes (echoes leading to signal generation after more than one refocusing pulse such as stimulated echoes) including differences in the signal intensities between even and odd echoes, thus, altering the single exponential nature of the $T_2$ decay observed in a single-echo spin-echo experiment. The indirect echoes are the result of refocusing pulses not attaining the ideal 180° flip angle (FA) due to nonrectangular slice profiles, static ($B_0$) and transmit field ($B_1$) inhomogeneity, and $B_1$ calibration errors (17).

To alleviate the pulse imperfection due to nonrectangular slice profiles, a thick refocusing slice technique has been proposed by Pell et al. (5). This technique employs a refocusing slice that is thicker than the excitation slice. $B_0$ and $B_1$ inhomogeneity, and calibration errors, however, are not corrected for by this approach. Echo editing techniques that use crusher gradients around the refocusing pulses have also been proposed to reduce the signal resulting from pathways leading to indirect echoes (18-20). However, not all pathways can be crushed effectively and the method has only been demonstrated with non-selective refocusing pulses, which limits the use of the method to single slice applications. Recently, Lebel and Wilman proposed the slice-resolved extended phase graph (SEPG) fitting algorithm (17), for accurate $T_2$ estimation from MESE data contaminated by indirect echoes. Their method is based on the extended phase graph (EPG) model proposed by Hennig (21) which provides decay curves for any given refocusing FA. The EPG model assumes perfectly rectangular slice profiles whereas the SEPG model includes the known slice profile for both excitation and refocusing pulses. The fitting algorithm fits the measurements to the SEPG model to obtain the $T_2$ estimates. The method is robust to $B_1$ inhomogeneity and calibration errors and it has been shown that accurate $T_2$ estimation can be obtained from MESE data acquired with reduced FAs (<180°).

So far, the SEPG fitting algorithm has been demonstrated for fully sampled or 60% partial k-space Cartesian data. The main limitation of combining the SEPG fitting algorithm with a model-based reconstruction approach for $T_2$ estimation from highly undersampled data (<10% sampled with respect to Nyquist sampling theorem), is the non-linearity of the SEPG model. Therefore it can be appreciated that there is a significant need for a technique to provide proper fitting with highly undersampled data. The present disclosure provides this and other advantages as will be apparent from the following detailed description and accompanying figures.

BRIEF DESCRIPTION OF THE SEVERAL VIEWS OF THE DRAWING(S)

FIG. 5 is a data table illustrating the percent error of $T_2$ estimates for phantom data acquired with standard sampling for various FA.

FIGS. 6A-6B illustrate the errors in the decay curves of the three phantom tubes illustrated in FIG. 4 but acquired with a high degree of undersampling (4% relative to the Nyquist condition).

FIG. 7 illustrates a data table showing the percent error of $T_2$ estimates for highly undersampled data that correspond to the same physical phantom used in FIGS. 4-6 where the percent errors are relative to the gold standard.

FIG. 11 is a data table illustrating the percent error of $T_2$ estimates for the phantoms acquired with the liver data illustrated in FIG. 10 in which the $T_2$ curves were reconstructed from undersampled data (4% sampled with respect to the Nyquist criteria) using REPCOM and the processing of the present disclosure.

FIG. 15 is a data table illustrating the results from a physical phantom showing the percent error in $T_2$ estimates for various fitting algorithms for both a tight and expanded region of interest.

FIG. 16 is a data table illustrating the results from a physical phantom showing $T_2$ estimates for the fitting processing described herein using highly undersampled data.

DETAILED DESCRIPTION OF THE INVENTION

Figure 1:
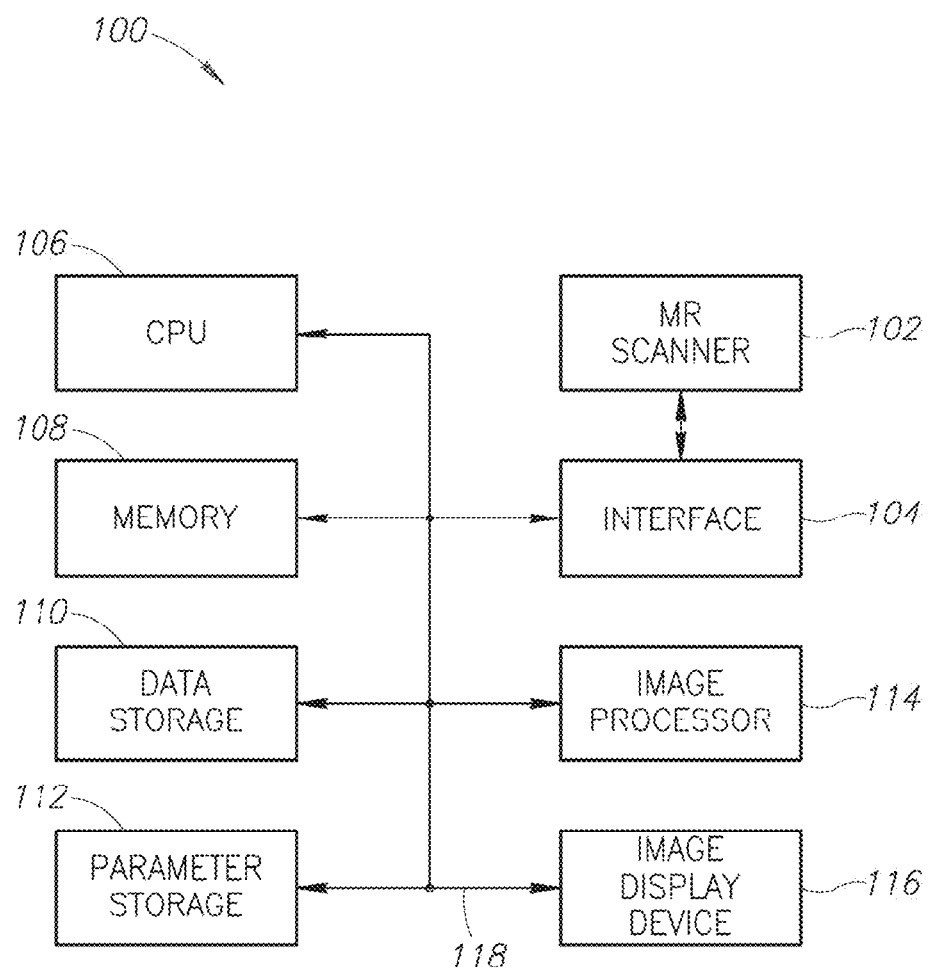
FIG. 1 is a block diagram of an exemplary system used to implement the techniques of the present disclosure.

The present disclosure is directed to a novel reconstruction technique for the estimation of the $T_2$, or spin-spin relaxation time, using highly undersampled MRI data acquired with a fast spin-echo (FSE) pulse sequence. The FSE sequence has the advantage that data acquisition is fast and that the temporal data sets used for calculating the $T_2$ maps are registered by the nature of the acquisition. As used herein, highly undersampled data refers to a sampling rate that is significantly less than the conventional Nyquist sampling rate criteria. For example, highly undersampled data may be in the range of 4-10% sample rate compared to the Nyquist sampling criteria. The highly undersampled data permits faster $T_2$ mapping; the use of a radial k-space trajectory allows for greater flexibility in the reconstruction of $T_2$ maps. A drawback of the FSE acquisition is the presence of indirect echoes which introduce errors in $T_2$ estimation when the signal is modeled by an exponential curve. The SEPG model, proposed by Lebel et al, is a better representation of the $T_2$ signal decay in the presence of indirect echoes. (17) However, the high non-linearity of the SEPG model impairs the reconstruction of $T_2$ maps when highly undersampled data are used.

The techniques described herein use a principal-component analysis (PCA) approach to linearize the SEPG signal and use an iterative reconstruction approach which incorporates the principles of compressed sensing (CS) to recover $T_2$ maps from highly undersampled data with indirect echo compensation. The results are accurate $T_2$ maps obtained from data with high temporal and spatial resolution from data acquired is a short period of time (e.g., breath hold). This is particularly important for $T_2$ mapping in areas in the body affected by motion, such as the abdomen and thoracic cavity.

The idea of using a linear approximation to the signal model together with CS to reconstruct parameter maps from highly undersampled data can be extended beyond the SEPG model and the FSE acquisition sequence. In general, signal models could be based on the Bloch equations.

While the example presented herein utilizes principal components as a linear approximation however, this is just one possibility. Other approximations can be used such as dictionaries, manifolds, and the like.

Those skilled in the art will appreciate that the linearized approach does not directly yield a parameter map, but coefficient maps from which the parameter can be estimated. This provides significant flexibility for the fitting of the data. For example, a least squares fitting approach can be used to obtain the parameter maps. More complex methods such as algorithms that deal with partial volume effects (caused by multiple components within a voxel) can also be used. In one embodiment, the fitting of parameters in multi-component systems can be significantly improved by using a joint estimation algorithm described herein. The joint estimation processing described below was developed with the goal of estimating parameter maps for small lesions embedded in an organ where partial volume effects are more pronounced. Characterizing small lesions is particularly important for early detection of cancer.

In one embodiment, it is possible to extend the RCA approach used in the REPCOM algorithm to linearize the SEPG model. The CUrve Reconstruction via pca-based Linearization with Indirect Echo compensation (CURLIE) technique described herein aims to obtain accurate $T_2$ decay curves from highly undersampled data in the presence of $B_1$ imperfections or non-180° refocusing pulses. The $T_2$ values of the reconstructed curves can then be obtained by applying SEPG fitting. Although only radial data is used in this work, the methodology can be translated to other trajectories.

Hennig's ERG model provides a way to calculate the signal intensity of a specific echo point for MESE sequences with the assumption that all spins experience the same FA. Given the excitation pulse FA, $\alpha_0$, the FAs of the N refocusing pulses, $\alpha_j$ (j=1, ..., N), the sensitivity of transmit $B_1$ field, and the $I_0$, $T_1$ and $T_2$ values of a voxel, the signal intensity at the $j^{th}$ spin echo, $S_j$, can be expressed as according to ref. 21:

$$S_j = I_0 \cdot \text{EPG}(T_1, T_2, B_1, \alpha_0, \ldots, \alpha_j, j). \quad [1]$$

The function $\text{EPG}(\cdot)$ does not have an explicit expression, but can be computed numerically. Based on the ERG model, Lebel and Wilman recently proposed the SEPG model (17). With the prior knowledge of the prescribed slice profile of the excitation pulse along the z direction, $\alpha_0(z)$, the prescribed slice profiles of the refocusing pulse along the z direction, $\alpha_j(z)$ ($j=1, \ldots, N$), the SEPG model can be obtained by integrating the EPG model throughout the slice:

$$C_j(I_0, T_1, T_2, B_1, \alpha_0(z), \ldots, \alpha_j(z)) = \quad [2]$$
$$I_0 \cdot \int_z \text{EPG}(T_1, T_2, B_1, \alpha_0(z), \ldots, \alpha_j(z), j) dz.$$

The SEPG fitting algorithm fits $T_2$ decay curves acquired with a MESE sequence to Equation [2]. Given N TE measurements $s_j$ ($j=1, \ldots, N$), the SEPG fitting algorithm can be written as:

$$I_0, T_1, T_2, B_1 = \quad [3]$$
$$\operatorname{argmin}_{I_0, T_1, T_2, B_1} \left\{ \sum_{j=1}^{N} \|C_j(I_0, T_1, T_2, B_1, \alpha_0(z), \ldots, \alpha_j(z)) - s_j\|^2 \right\}.$$

In Ref. 17, it has been shown that the SEPG model is insensitive to $T_1$ values when $T_1/T_2$ ratio is large, hence it has been proposed to fix $T_1$ to $\infty$ in order to simplify the signal model and the fitting algorithm:

$$C'_j(I_0, T_2, B_1, \alpha_0(z), \ldots, \alpha_j(z), j) = \quad [4]$$
$$I_0 \cdot \int_z \text{EPG}(T_1 = +\infty, T_2, B_1, \alpha_0(z), \ldots, \alpha_j(z), j) dz,$$

$$I_0, T_2, B_1 = \operatorname{argmin}_{I_0, T_2, B_1} \quad [5]$$
$$\left\{ \sum_{j=1}^{N} \|C'_j(I_0, T_1 = +\infty, T_2, B_1, \alpha_0(z), \ldots, \alpha_j(z)) - s_j\|^2 \right\}.$$

In the published work of the SEPG fitting algorithm, the amplitude images were obtained from fully or 60% sampled Cartesian k-space. For highly undersampled data (<10% sampled), the fitting algorithm relies on a reconstruction algorithm which can accurately recover the decay curves. Thus, it is intuitive to combine the SEPG model with a model-based algorithm (11, 22):

$$I_0, T_2, B_1 = \operatorname{argmin}_{I_0, T_2, B_1} \quad [6]$$
$$\left\{ \sum_{j=1}^{N} \|FT\{C'_j(I_0, T_1, T_2, B_1, \alpha_0(z), \ldots, \alpha_j(z))\} - K_j\|^2 \right\},$$

where $I_0, T_2, B_1$ are the vectors of $I_0, T_2, B_1$ of all voxels, FT is the forward Fourier transform, $K_j$ is the (undersampled) k-space data acquired at the $j^{th}$. Due to the large dimensionality of the problem, it is impractical to use a global minimization algorithm to solve Equation [6], hence a local minimization algorithm (such as the gradient-based minimization algorithm) can be used. However, the SEPG model is non-linear as a function of $T_2$ and $B_1$ and it is difficult to obtain the gradient for minimization purposes.

In the REPCOM algorithm (12), we use PCA to linearize the exponential $T_2$ decay model, thus overcoming non-linear minimization problems. In CURLIE we extend the PCA approach to approximate the SEPG model. The principal components (PCs) are calculated for given TE points using a training set of decay curves given by the SEPG model for a certain range of $T_2$ and $B_1$ values. With the PCs obtained from the training curves, the $T_2$ decay curves with indirect echoes can be approximated by a weighted linear combination of the PCs.

Let $\vec{v}$ be a vector representing a noiseless $T_2$ decay curve with indirect echoes. Let $L$ be the number of PCs to be used in the approximation and $\vec{p}_i$, the $i^{th}$ PC vector, $\vec{v}$ can be approximated by a linear combination of $\vec{p}_i$:

$$\vec{v} = \sum_{i=1}^{L} m_i \vec{p}_i, \quad [7]$$

where $m_i$ is the weighting of the $i^{th}$ principal component. $\hat{P} = (\vec{p}_1, \vec{p}_2, \ldots, \vec{p}_L)$ is the matrix consisting of the vectors of the first $L$ PCs. $M = (\vec{M}_1, \vec{M}_2, \ldots, \vec{M}_L)$ Let $\vec{M}_i$ be the vector of $m_i$ for all the voxels and M can be formed as $(\vec{M}_1, \vec{M}_2, \ldots, \vec{M}_L)$. Let $\hat{B}_j \hat{P}_j$ denote the row of the matrix $\hat{P}$. Note that $M \hat{B}_j^T M \hat{P}_j^T$ yields the image at $TE_j$ from the $L$ principal component coefficients. Equation [6] can be reformulated as:

$$\hat{M} = \arg \min_M \{ \sum_{j=1}^{L} \|FT_j(M\hat{P}_j^T) - \vec{K}_j\|^2 \}. \quad [8]$$

When the complex coil sensitivity profiles $S_i$ and the sparsifying penalties $\text{Penalty}_i(\cdot)$ (with corresponding weights $\lambda_i$) are given (12), the algorithm can be written as:

$$\hat{M} = \arg \min_M \{ \sum_{i=1}^{\# \text{coils}} \sum_{j=1}^{L} \|FT_j(S_i M \hat{P}_j^T) - \vec{K}_{i,j}\|^2 + \sum_i \lambda_i \text{Penalty}_i(M) \}. \quad [9]$$

The penalty terms are used to exploit the spatial compressibility of the PC coefficient maps in the framework of compressed sensing and have been shown to improve the quality of the reconstructed $T_2$ maps (12). The decay curves are reconstructed from $\hat{M}$ which can be obtained by a conjugate gradient minimization algorithm.

The SEPG fitting algorithm (Equation [5]) can then be applied to the curves reconstructed by CURLIE to obtain $T_2$ estimates. As mentioned above, Lebel and Wilman proposed to fix the $T_1$ to be $+\infty$ for the fitting (17). As an alternative, an optimized $T_1$ value can be used in the SEPG fitting based on the prior knowledge of the anatomy being imaged as indicated by Sénégas et al. (23).

FIG. 1 is a functional block diagram illustrating an exemplary embodiment of a system 100 used to perform the image processing described herein. A magnetic resonance (MR) scanner 102 is used to acquire the imaging data. The MR scanner 102 is coupled to an interface 104. The interface 104 provides instructions and control information to the MR scanner 102 and receives imaging data from the MR scanner.

The system 100 also includes a central processing unit (CRU), which may be a conventional micro-processor, a customized micro-processor, digital signal processor, or the like. The system is not limited by the specific form of implementation of the CPU 106.

The system 100 also includes a memory 108, which may include random access memory, read-only memory, flash memory, and the like. A portion of the memory 108 may be implemented integrally with the CPU 106. In general, the memory 108 stores data and provides instructions to the CPU 106 for processing the stored data.

The system 110 also includes data storage, which may be implemented as a portion of the memory 108 or a stand-alone data storage, such as a magnetic disk drive, tape drive, optical storage device, or the like. As will be described in greater detail below, the data storage 110 may store the imaging data received from the MR scanner 102 via the interface 104.

The system 100 also includes a parameter storage 112. The parameter storage 112 may include data, such as the spin-echo pulse sequences. The parameter storage 112 may also store modeling data for reconstruction.

The system 100 also includes an image processor 114 that will process the image data in accordance with the processing techniques described herein. Those skilled in the art will appreciate that the image processor 114 may be a stand-alone processor or part of the CPU 106 executing instructions from the memory 108 to perform the functions of the image processor 114. The image processor 114 is illustrated in the functional block diagram of FIG. 1 as a separate component because it performs a separate function.

The system 100 also includes an image display device, which may be a computer monitor or other conventional output device, such as a printer.

Various components of the system 100 are coupled together by a bus system 118. The bus system 118 may include an address bus, data bus, power bus, control bus, and the like. For the sake of clarity, those various busses are illustrated in FIG. 1 as the bus 118.

Figure 2:
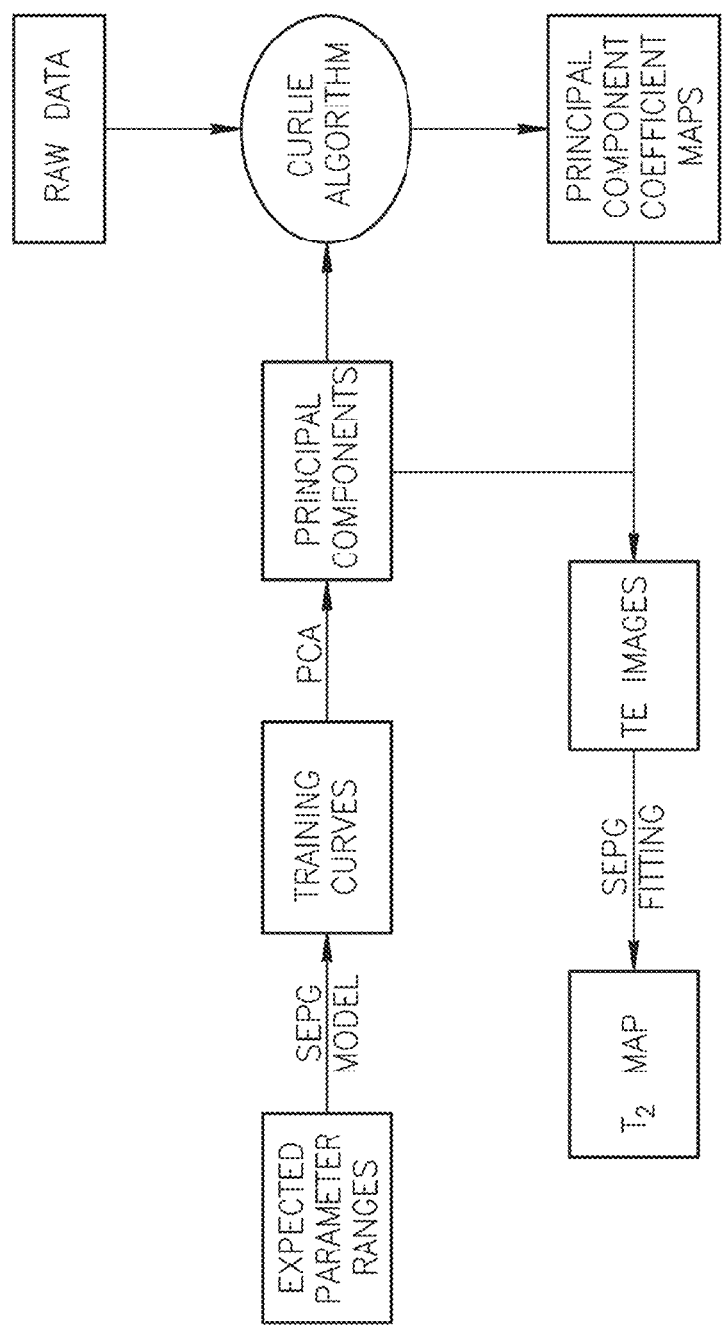
FIG. 2 is a flow chart illustrating the signal processing by the system of FIG. 1.

The flow chart of the CURLIE reconstruction algorithm and the SEPG fitting is shown in FIG. 2. Different from REPCOM, the new method includes the effects of indirect echoes in the $T_2$ estimation process by incorporating the SEPG model in the generation of the training curves and in the estimation of the principal components coefficients (via the CURLIE algorithm) as well as in the fitting of the TE images to obtain the final $T_2$ map.

Methods

All radial MESE data were acquired on a 1.5 T Signa HDxt GE (General Electric Healthcare, Milwaukee, Wis.) MR scanner 102 using a previously developed radial fast spin-echo (radFSE) pulse sequence (24). A "bit-reversed" angular ordering was used to minimize artifacts from $T_2$ decay and motion (25). The slice profiles of the excitation and refocusing pulses were generated from the Fourier transform of the radio frequency waveforms provided by the manufacturer for fast-spin echo pulse sequences. The refocusing slice radio frequency profiles are calibrated by the techniques in Ref. 26. It should be noted that in the manufacturer's pulse sequence the full-width half-maximum of the refocusing pulses is designed to be about 1.6 times as thick as the corresponding excitation pulse.

Computer Simulation

Curves were generated according to the SEPG model assuming an ETL=16 and echo spacing=12.11 ms with the slice discretized into 63 points along the slice profile. A total of 765 curves were generated for $T_2$ values varying from 50 ms to 300 ms with a step size of 5 ms, $B_1$ values varying from 0.5 to 1.2 with a step size of 0.05, and $T_1 = +\infty$. The PCs were trained from these 765 curves.

Phantom Data

A physical phantom, containing three 10 mm glass tubes filled with $MnCl_2$ solutions of different concentrations (50 μM, 75 μM, and 170 μM) to yield data at different $T_2$'s, was prepared. RadFSE data were acquired with a single channel transmit/receive coil, with an echo train length (ETL) of 16 with echo points spaced by 12.11 ms, TR=1 s, excitation slice thickness=8 mm, receiver bandwidth=±15.63 kHz, field of view (FOV)=10 cm. The acquisition matrix for undersampled data was 256×256 yielding 16 radial k-space lines for each of the 16 TE data sets. For comparison purposes, another data set was acquired with an acquisition matrix of 256×4096 to yield 256 radial k-space lines for each TE; all other acquisition parameters were kept the same. Although for radial acquisition a data set with 256 radial lines and 256 sampling points per line is 64% sampled (according to the Nyquist theorem a fully sampled data set requires 402 radial lines for 256 sampling points per line), the data set gives good quality images and accurate $T_2$ maps for most clinical applications (as well as for our phantom work). In this work, this data set is referred to as "standard sampled."

Cartesian single-echo spin-echo data (not contaminated by indirect echoes) of the phantom were also acquired to obtain the gold standard $T_2$ values. Data were acquired with a single channel transmit/receive coil, TR=5 s, excitation slice thickness=8 mm with the refocusing slice being approximately 5 times as thick as the excitation slice, receiver bandwidth=±15.63 kHz, and FOV=10 cm, Data for 4 TE points (12, 24, 36 and 48 ms) were acquired with the acquisition matrix per TE point set to 64×64. A lower resolution was used for the single-echo spin-echo sequence due to its long acquisition time. Gold standard $T_2$ values were obtained by fitting the data to a single exponential decay.

In Vivo Data

Each in vivo data set (brain, liver and heart) were acquired from a separate volunteer under informed consent with a protocol approved by the local Institutional Review Board.

In vivo brain data were acquired using the radFSE pulse sequence with an 8-channel receiver head coil, 16 TE points equispaced by 12.93 ms, excitation slice thickness=8 mm, receiver bandwidth=±15.63 kHz, TR=4 s, and FOV=24 cm. The acquisition matrix for the standard sampled data set was 256×4096 to yield 256 radial lines per TE. The acquisition matrix for the undersampled data set was 256×512 yielding 32 radial lines per TE (8.0% sampled compared to fully sampled data). Experiments were conducted with the refocusing radio frequency pulses FAs prescribed to be 180° and 120°.

In vivo liver data were acquired in a breath hold using the radFSE pulse sequence with an 8-channel receiver torso coil, 16 TE points equispaced by 8.93 ms, slice thickness=8 mm, receiver bandwidth=±31.25 kHz, TR=1.5 s, FOV=48 cm, and acquisition matrix=256×256 to yield 16 radial lines per TE (4.0% sampled compared to fully sampled data). To evaluate the estimated $T_2$ values, three tubes containing either $MnCl_2$ or agarose for $T_2$ variation were placed on the subject's chest. The gold standard $T_2$ values of the three tubes were estimated to be 56.0 ms, 77.9 ms and 64.0 ms in a separate experiment using a single-echo spin-echo sequence.

In vivo cardiac data were acquired using a radFSE pulse sequence which included a double-inversion preparation period for nulling the signal from flowing blood (27). Data were acquired with an 8-channel receiver cardiac coil, 16 TE points equispaced by 9.46 ms (for refocusing pulses with prescribed FA=180°) or 6.85 ms (for refocusing pulses with prescribed FA=155°), slice thickness=8 mm, receiver bandwidth=±31.25 kHz, TR=1 RR, and FOV=48 cm. The acquisition matrix was 256×256 resulting in 16 radial lines per TE (4.0% sampled compared to fully sampled data). Imaging of a slice was completed within a breath hold (~15-18 s).

Data Reconstruction

All algorithms were implemented in Matlab (MathWorks, Natick, Mass.). The training curves for PC ($\hat{P}$) generation were provided by the SEPG signal model using Equation [3]. Equation [8] was solved iteratively by using the non-linear Polak-Ribiere Conjugate Gradient algorithm (28). The spatial penalty terms used in Equation [9] consisted of the 1-norms of the wavelet transform (Daubechies 4, code obtained from http://www-stat.stanford.edu/~wavelab) and total variation of the PC coefficient maps.

$T_2$ estimates were obtained either by conventional exponential fitting or by SEPG fitting. SEPG fitting was performed using Equation [4]; during the fitting, $T_2$ was allowed to vary between 30-5000 ms and $B_1$ was limited to 0-3. The $T_1$ values used in the SEPG fitting were fixed to an optimal value using prior information. For each in vivo image a single $T_1$ was chosen based on reported values for the anatomy of interest: gray matter for brain (950 ms) (29), liver (500 ms) (30) and myocardium (700 ms) (31). For the phantom data, where there was a wide range of $T_1$ values among the different vials used, the optimal $T_1$ was determined as proposed in Ref. 23. In brief, a set of simulated curves were generated using the SEPG model with $T_1$, $T_2$, and $B_1$ varying independently between 300-2000 ms, 50-300 ms, and 0.5-1.2, respectively. SEPG fitting was then performed on these curves for each of the $T_1$ values in the selected range. The $T_1$ value that minimized the $T_2$ estimation error according to the 2-norm was selected to be the optimized $T_1$.

For comparison, $T_2$ maps were also reconstructed using the REPCOM algorithm. The $T_2$ values for the PC training were between 35 ms to 300 ms equispaced by 1 ms. Total variation and wavelet transforms were used as the sparsifying transform with proper weightings as in Ref. 12.

Results

Proof-of-Concept

Figure 3A:
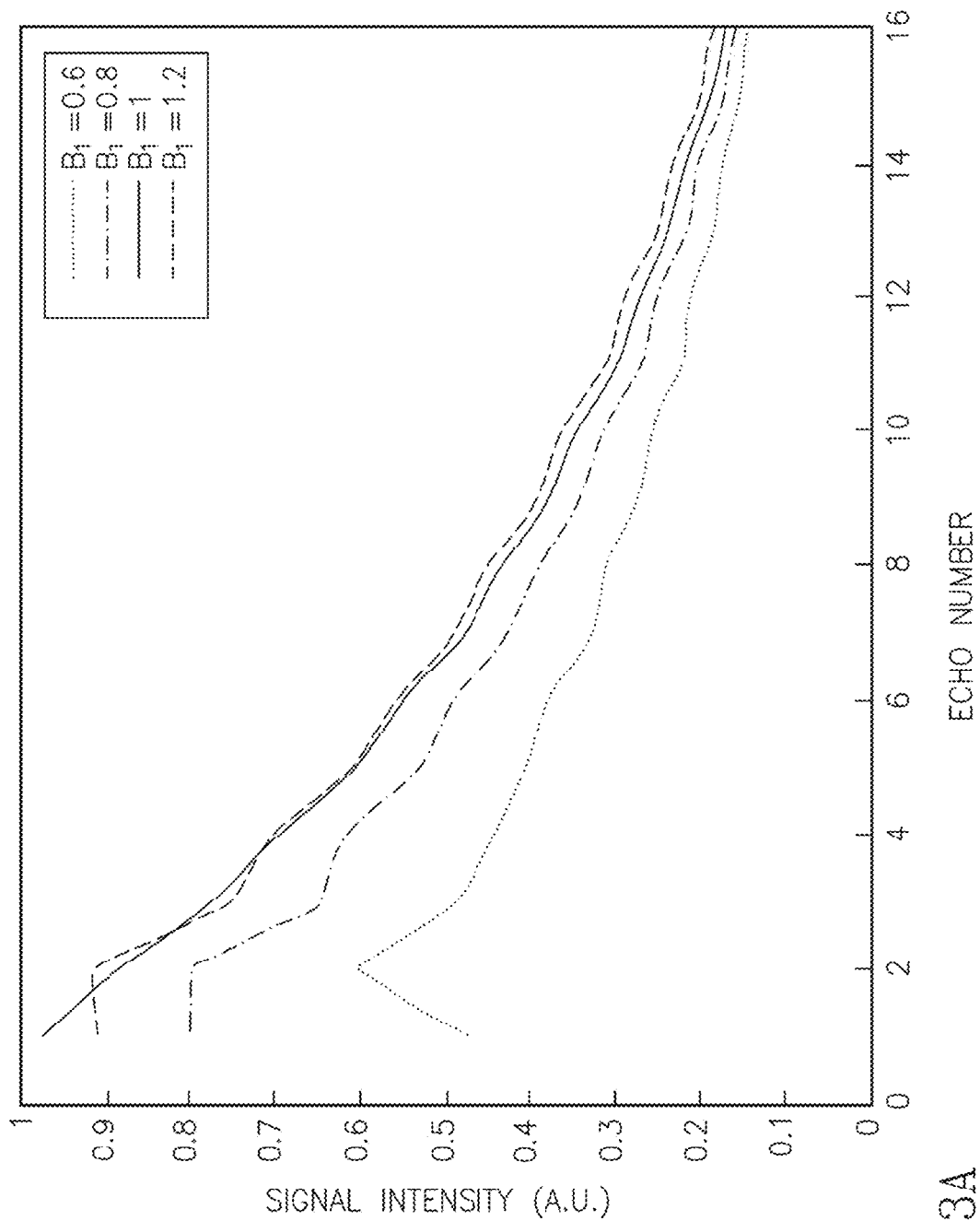
FIGS. 3A-3C are a series of graphs illustrating selected training curves, the approximation error for the training curves, and the distribution of the percentage of error caused by the approximation error.
Figure 3B:
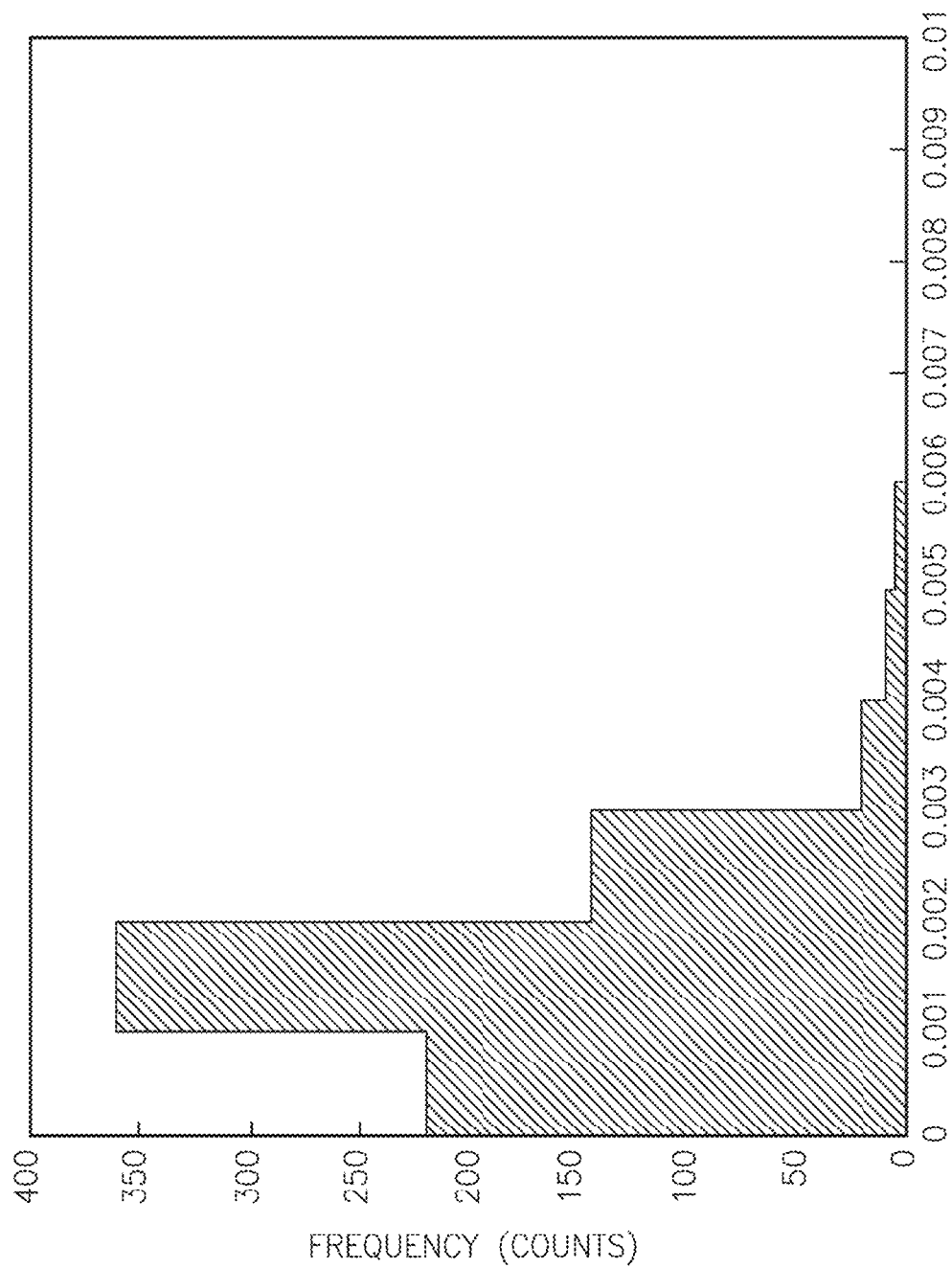
Figure 3C:
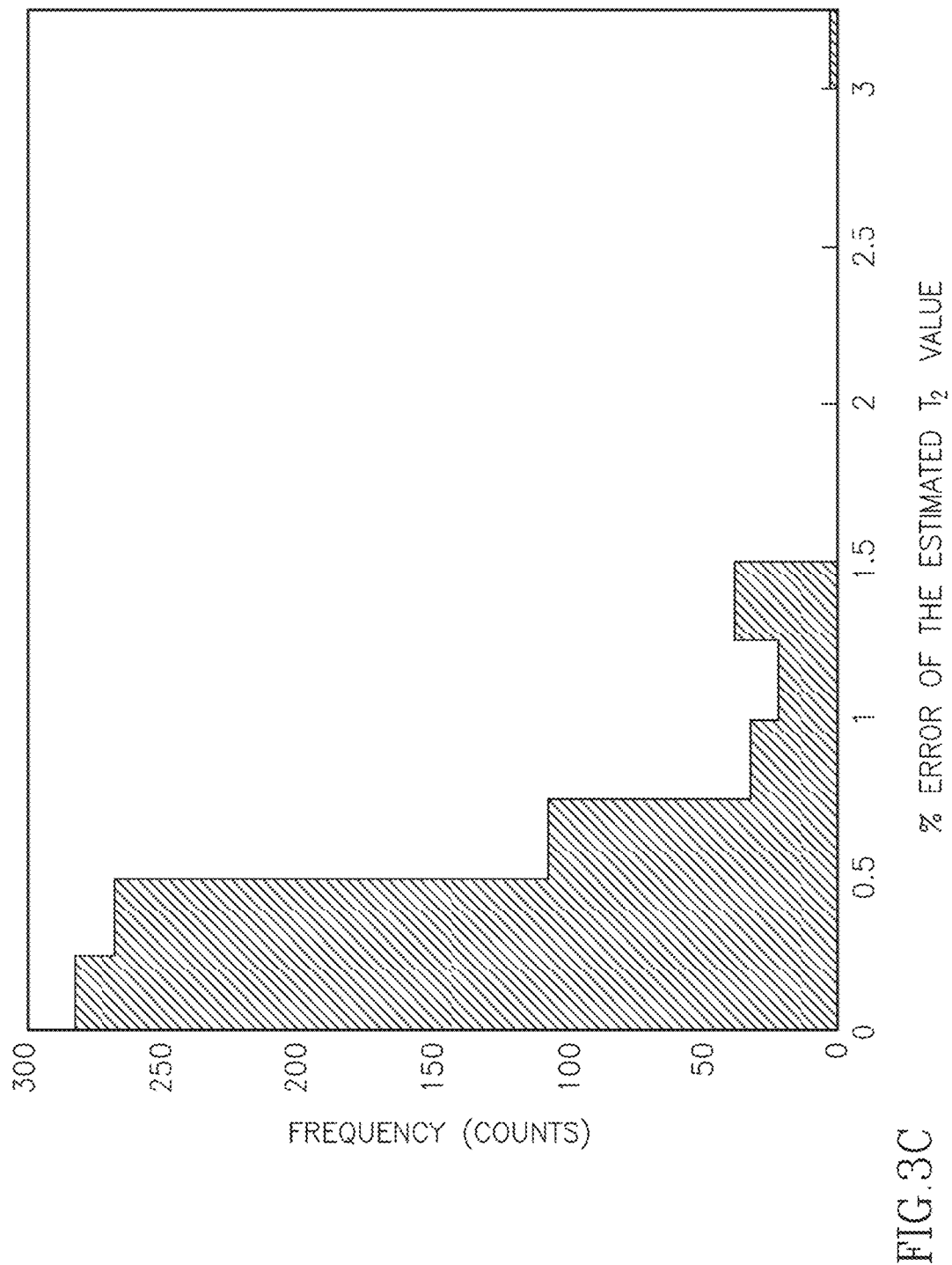
Figure 4A:
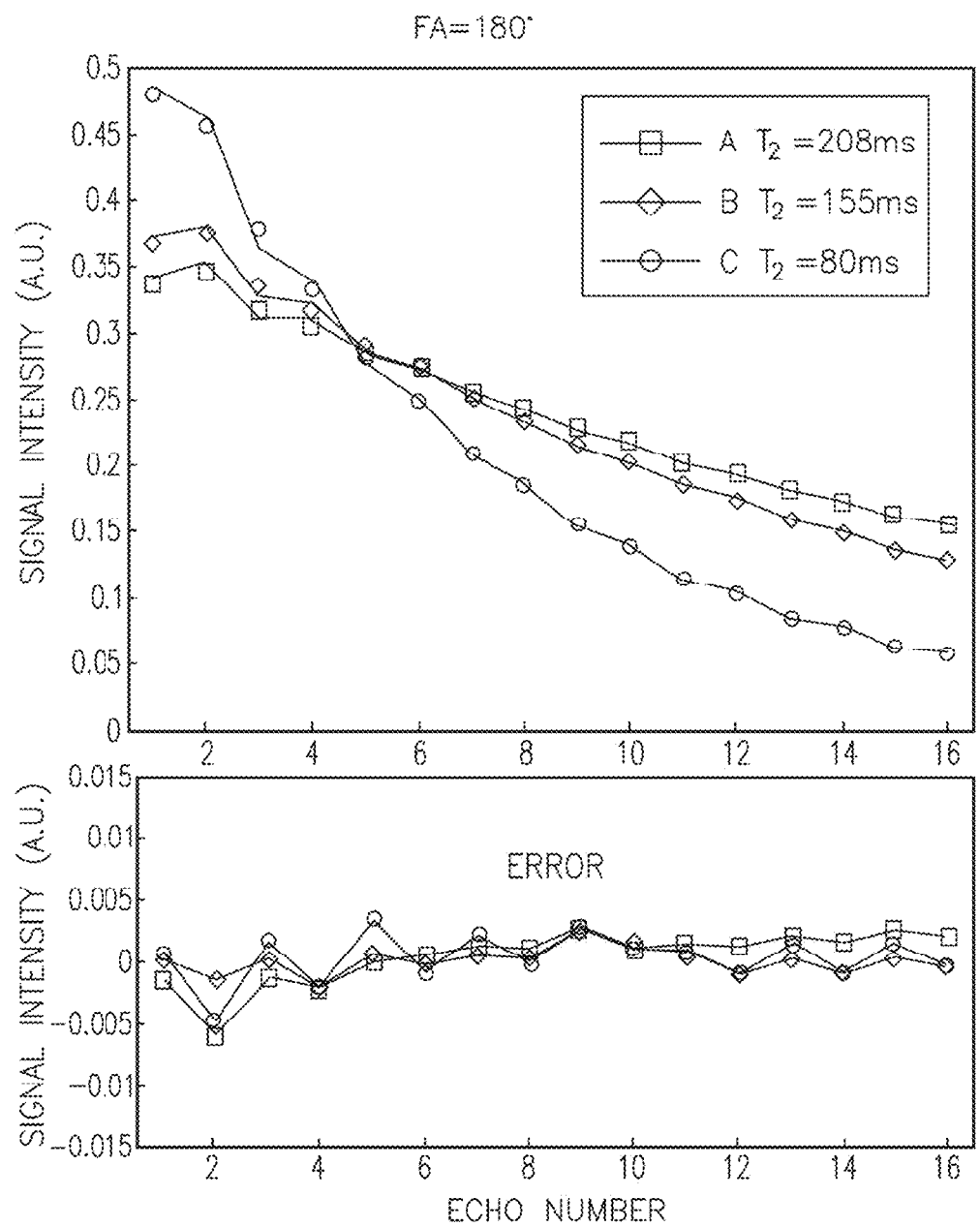
FIGS. 4A-4D illustrate the decay curves for phantom tube sample data acquired with different re-focusing flip angles (FA) and standard sampling (64% relative to the Nyquist condition).
Figure 4B:
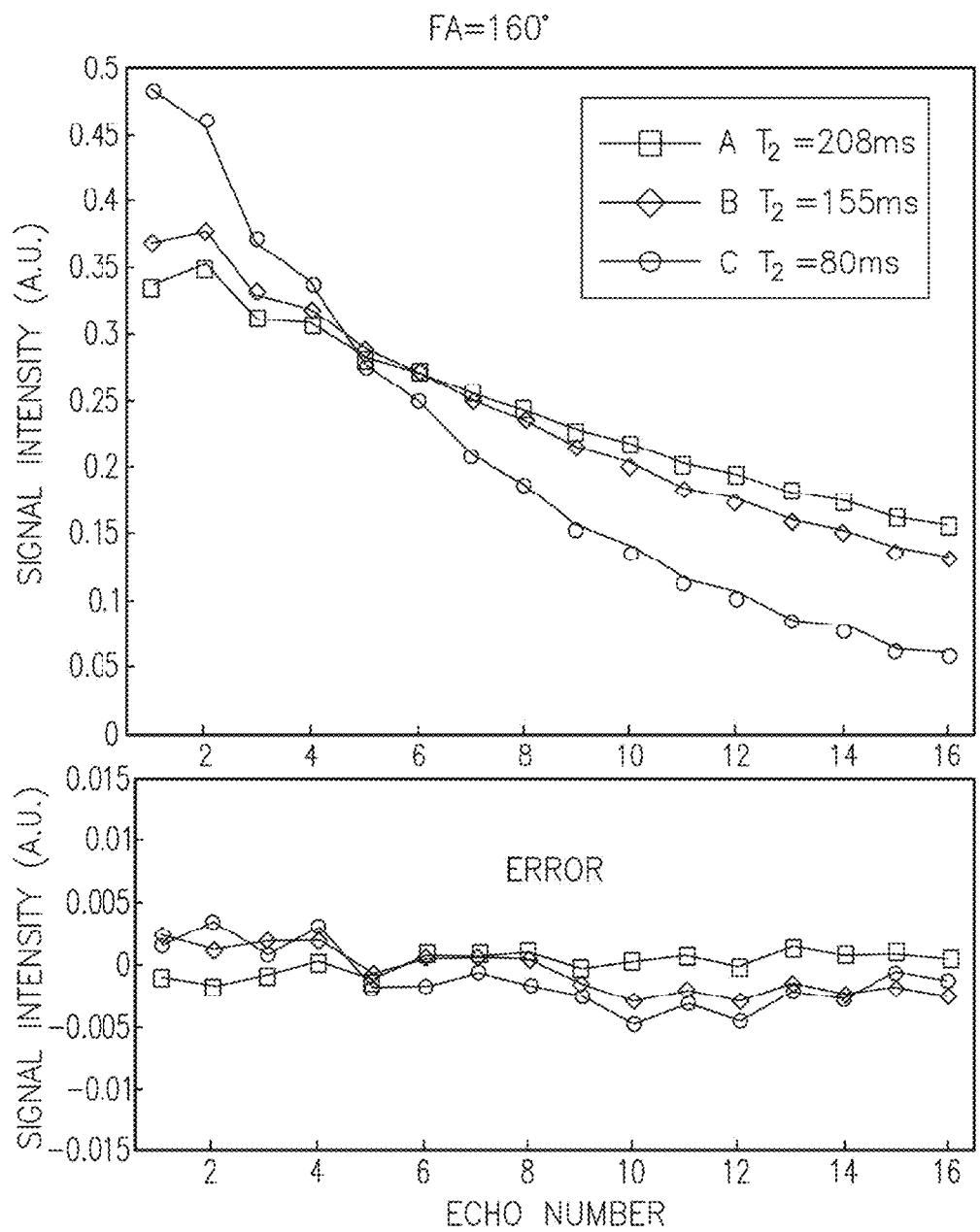
Figure 4C:
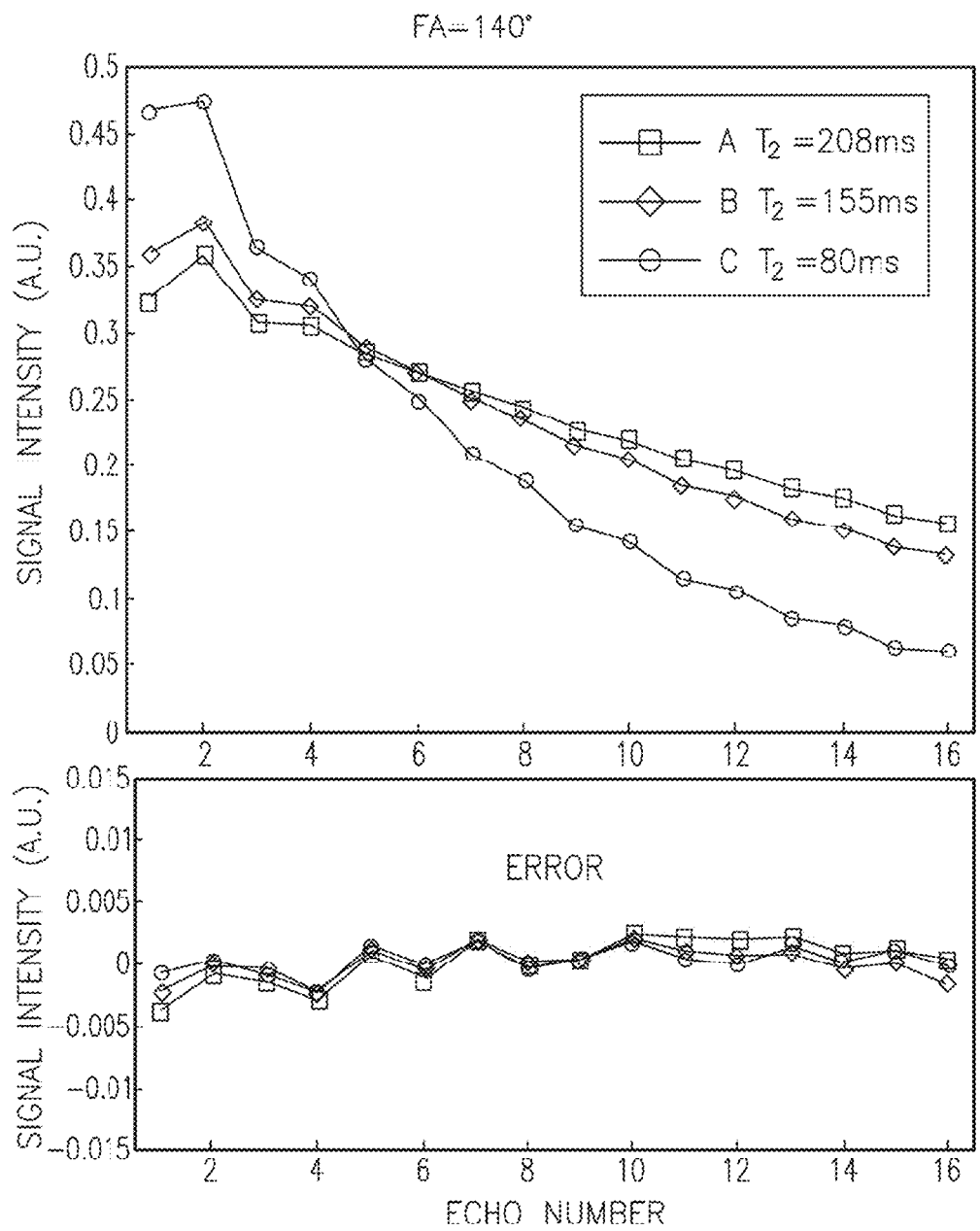
Figure 4D:
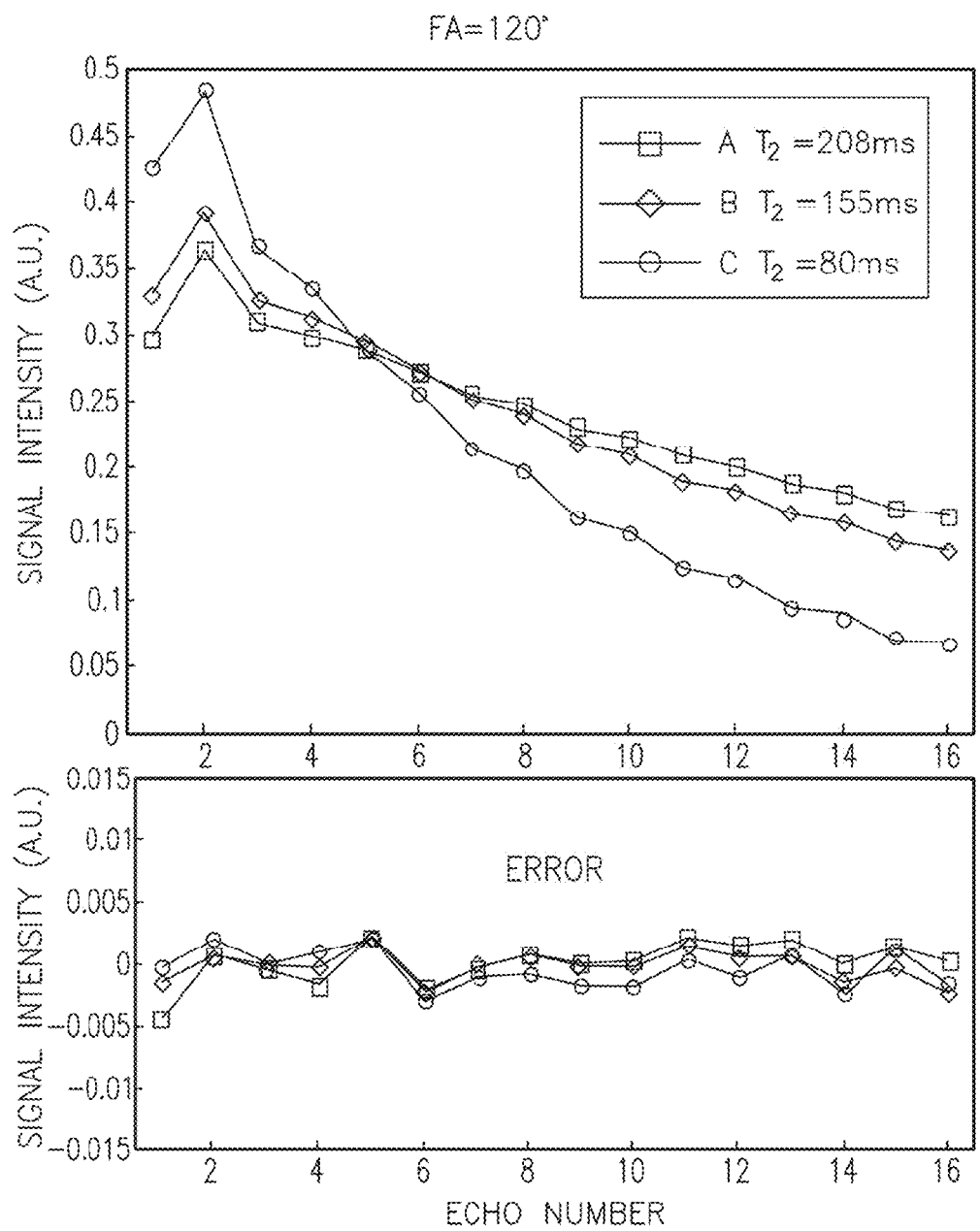

In order to demonstrate that a small number of PCs are sufficient to characterize the $T_2$ decay curves in the presence of indirect echoes, we first performed simulations. FIG. 3A shows four out of the 765 curves generated according to the SEPG model. FIG. 3A illustrates selected training curves for $T_2$=100 ms, $T_1$=+∞, and $B_1$ ranging from 0.6 to 1.2. The curves were simulated numerically using the SEPG model. An echo spacing of 12.1 ms was used in the simulations to cover a TE range similar to in vivo data. The curves show the expected signal modulation due to indirect echoes with modulations increasing with $B_1$. FIG. 3B shows the 2-norm of the approximation error when six PCs are used to represent the curves after these are normalized so that the 2-norm is unity. Note that the 2-norms of the approximation error are all below 0.006 and most of the errors have 2-norm<0.003. FIG. 3C shows the distribution of the % error of the $T_2$ values estimated by SEPG fitting caused by the PC approximation when six PCs are used to represent the training decay curves. As shown, the % errors in $T_2$ values estimated from the curves recovered from six PCs are all <3.5% with majority of the errors being <1.5%. These experiments show that it is sufficient to use $L$=6 to represent the training curves accurately under the given conditions and that the approximation error caused by using only the first six PCs is small. From our experience $L$ depended on the sample being imaged. In some cases using $L$=3 gave good results.

Experiments using physical phantom data were performed to further investigate the accuracy of the linear approximation using principal component decomposition. Phantom data were acquired with radFSE using standard sampled data (256 radial lines per TE with 256 points per radial line). FIGS. 4A-4D show decay curves reconstructed directly from the acquired data for each of the three phantom tubes shown in the image and for various refocusing FA. Each point in the decay curves corresponds to the averaged signal from voxels within a region of interest (ROI) for each tube. Each curve is the fitted decay curve according to the SEPG model from fitting parameters using the SEPG fitting ($T_1$=+∞). The curves are normalized (2-norm=1). As shown, the fitted curves are well matched to the acquired data for all the four FAs. FIGS. 4A-4D show the approximation error of the corresponding curves recovered from the six PCs used to generate FIGS. 3B-3C. The errors are all below 0.01 with most under 0.005. The 2-norms of the approximation error are between 0.0018 and 0.0042 for all FAs which also show that six PCs can represent the decay curves of the acquired data well. Note that the same PCs were used for all FAs (FA changes are equivalent to $B_1$ changes under the model). In this experiment $T_1$ was not optimized and assumed to be +∞.

The accuracy of $T_2$ estimation is then evaluated using the curves recovered from six PCs using the standard sampled phantom data. The data in Table 1 of FIG. 5 compares the bias in $T_2$ estimates obtained from the "recovered curves" to those from curves obtained directly from the TE images ("original curves"). The data in the table of FIG. 5 corresponds to the vials in the physical phantom shown in FIG. 4 acquired with standard radial sampling (i.e., data for each TE time point as 256 radial lines with 256 points per line.) The table shows results for various FA and for three fitting algorithms; exponential fitting, SEPG fitting with $T_1$=+∞, and SEPG fitting with $T_1$ optimized. The percentage errors are relative to the gold standard. It can be observed that for each fitting algorithm the bias of $T_2$ estimates obtained from the original and recovered curves are very similar. The differences in $T_2$ bias are all below 0.3%, which further demonstrates the accuracy of the PC approximation for representing the acquired decay curves. The results also show that the exponential fitting of MESE data overestimates $T_2$ values. The estimation bias increases as $T_2$ increases and as the FA diverges from 180° due to the more pronounced indirect echo effect; for FA=120°, the bias of the exponential fitting can be up to 18.4% (with the larger bias for $T_2$=210 ms). The bias of the SEPG fitting with $T_1$=+∞ is less than 6% which is significantly smaller than the bias of the exponential fitting. When an optimized $T_1$ (500 ms) was used, the largest error is further reduced to 3.6% which demonstrates that the optimized $T_1$ can be used in the SEPG fitting to improve $T_2$ estimation.

$T_2$ Estimation from Highly Undersampled Data

Figure 6A:
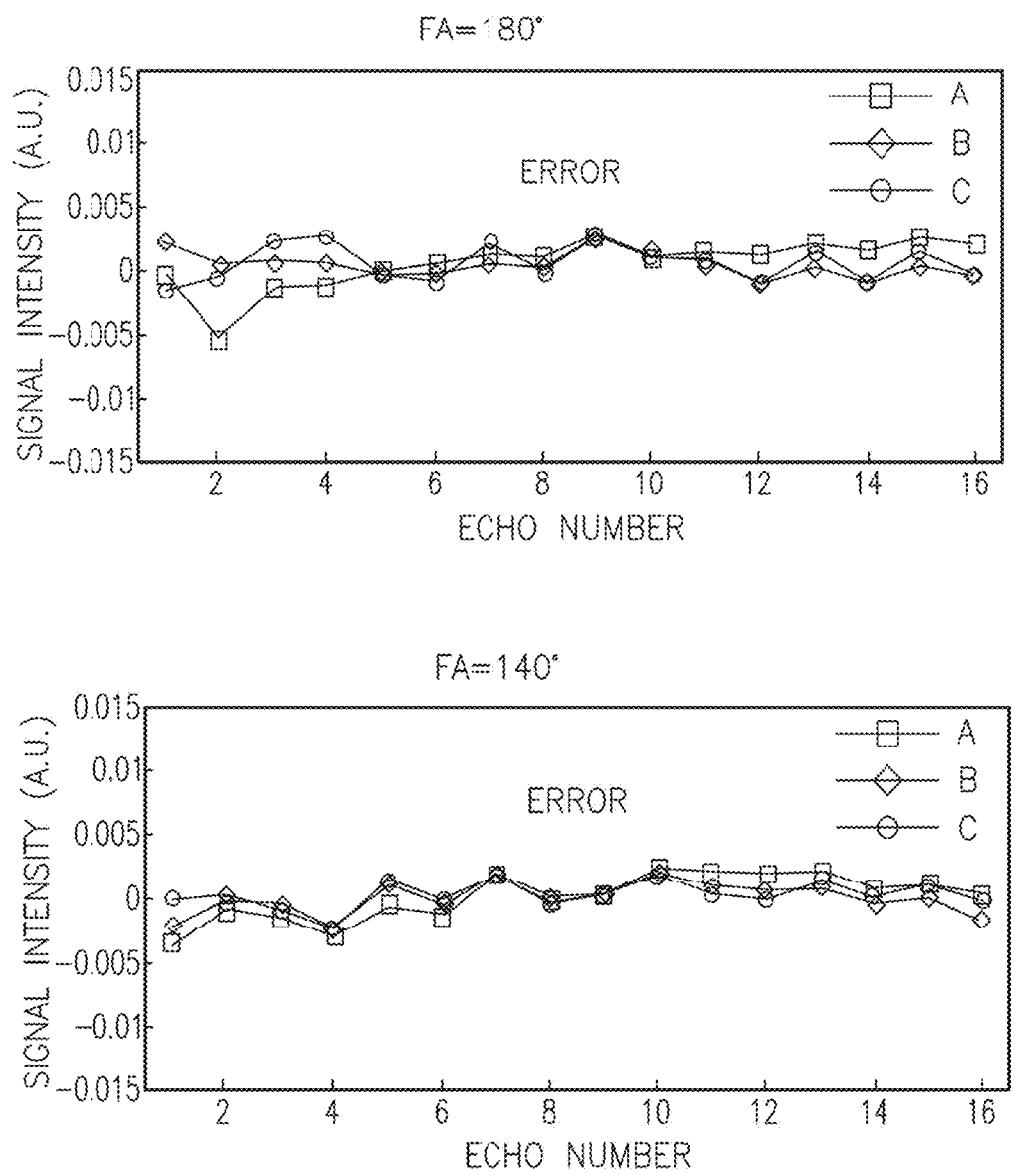

So far, we have demonstrated that a few principal components can accurately represent the $T_2$ decay curves contaminated with indirect echoes using standard sampled data. For highly undersampled data we need to use the CURLIE algorithm described in Equation [8], where the PCA-based signal model is used to match the acquired k-space data. Using the three-tube physical phantom and highly undersampled radFSE data (i.e., data with only 16 radial lines per TE) we tested the accuracy of CURLIE for reconstructing the decay curves using six PCs. FIGS. 6A-6B illustrate the difference between curves reconstructed from highly undersampled data using CURLIE and curves obtained from the standard sampled data (64% sampled) for various FAs. The highly undersampled data was 4% relative to the Nyquist criteria. In general, the differences between the curves are small despite the fact that the highly undersampled data has 16 times less samples than the standard sampled data. The 2-norms of the differences are between 0.0035 and 0.0095 which demonstrates that decay curves from highly undersampled data can be accurately reconstructed by CURLIE. The $T_2$ estimates for the three tubes in the phantom, obtained with SEPG fitting, are shown in Table 2, shown in FIG. 7. Note that the $T_2$ bias of undersampled data is similar to the $T_2$ bias obtained for standard sampled data (data from Table 1): less than 5% for $T_1=+\infty$ and less than 3.6% for $T_1=500$ ms. This demonstrates that the decay curves reconstructed by CURLIE from highly undersampled data have the same $T_2$ characteristics as the decay curves obtained from the standard sampled data.

Figure 8:
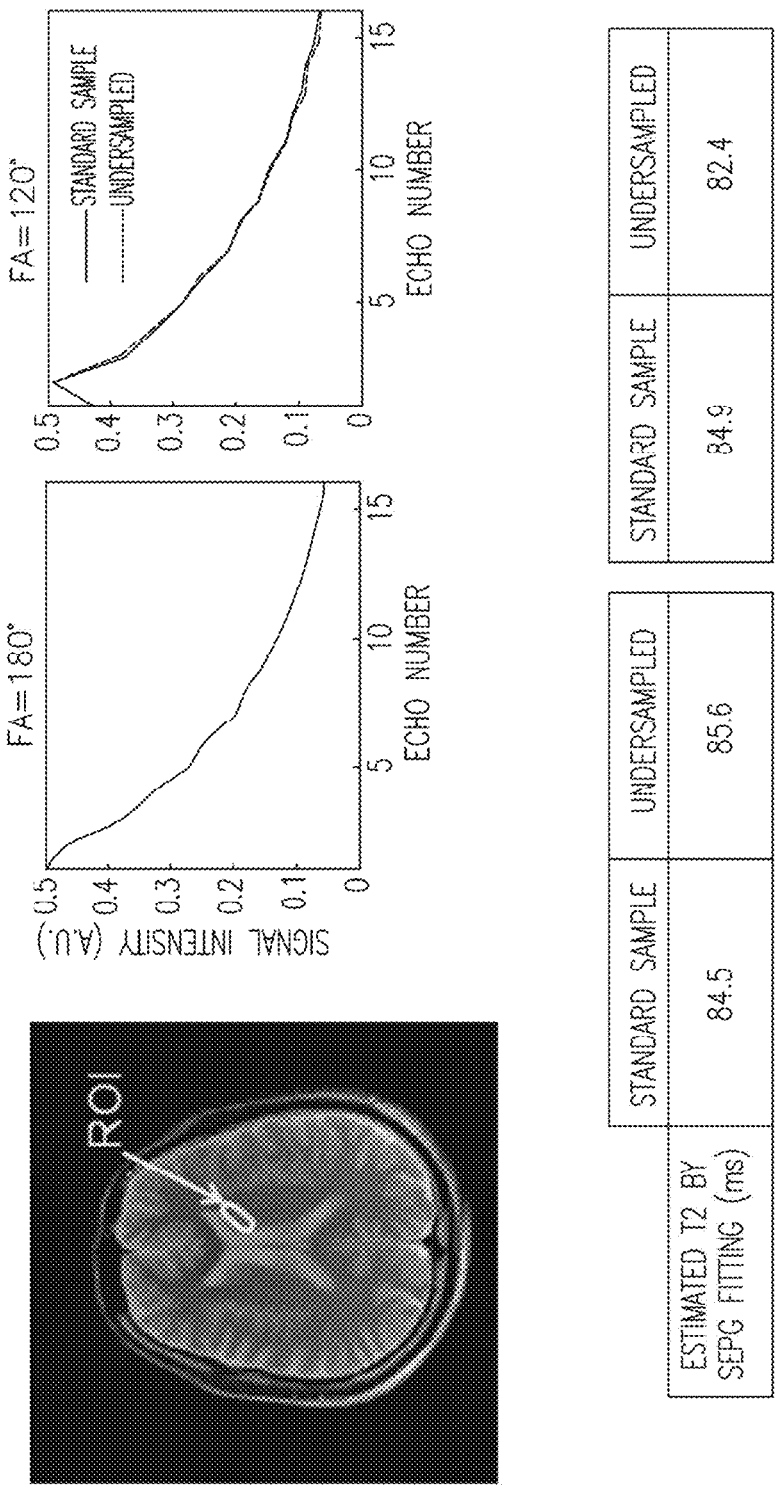
FIG. 8 illustrates an MRI image with a designated region of interest (ROI) and the decay curves and $T_2$ estimates of the ROI for different FA values.

CURLIE was tested in vivo using brain data. Two experiments were conducted: one where the prescribed FA of the refocusing pulses was 180°, another where the prescribed FA was 120°. The same six PCs used in Table 2 of FIG. 7 were used for the reconstruction of the undersampled brain data. In FIG. 8 the decay curves of the shown ROI obtained from standard sampled data (directly from the TE images) are compared to the curves reconstructed from 32 radial lines per TE (8.0% sampled) using CURLIE. Note that the curves generated from under- and standard sampled data are very similar (the error for all echo points for each of the two FA are below 0.01). The $T_2$ values obtained from the decay curves using SEPG fitting are also shown in the figure. The differences between the $T_2$ values obtained from under- and standard sampled data are below 3%. These results show that the curves reconstructed from highly undersampled in vivo data agree well with the decay curves obtained from standard sampled data. Also, note that the $T_2$ values estimated from data acquired with 180° and 120° FAs are similar.

Figure 9:
FIG. 9 shows an image of a $T_2$ map obtained using the present techniques and the % difference between $T_2$ maps obtained from data acquired with prescribed FAs of 180 and 120 using REPCOM (a technique which does not compensate for indirect echoes) and CURLIE with SEPG fitting with two different $T_1$ values.

A voxel-wise brain $T_2$ map obtained using CURLIE and SEPG fitting for data acquired with prescribed FAs of 180° is shown in FIG. 9A. FIG. 9B shows the difference map between data acquired with prescribed FAs of 180° and 120° but reconstructed with the REPCOM algorithm (i.e. where the training curves do not take into account indirect echoes and single exponential fitting is used for $T_2$ estimation). The % difference maps between $T_2$ maps obtained by CURLIE with SEPG fitting from data acquired with prescribed FAs of 180° and 120° is shown in FIGS. 9C and 9D for $T_1=+\infty$ and $T_1=950$ ms, respectively. The same six PCs as in previous figures were used for both FAs. In the % difference maps, the ventricles are masked out due to the fact that the $T_2$ of cerebrospinal fluid (~2000 ms) is much larger than the white and gray matter, and the TE coverage used here is not suitable for the accurate estimation of long $T_2$s. The means of the difference map are: 8.3% for the map derived from the REPCOM reconstruction and 4.9% and 3.1% for the maps derived from CURLIE and SEPG fitting with $T_1=+\infty$ and $T_1=950$ ms, respectively. The small means in the difference maps support the concept that the CURLIE reconstruction followed by SEPG fitting significantly reduces the effect of indirect echoes in $T_2$ estimation in vivo. When an optimized $T_1$ is used in the SEPG fitting the % difference $T_2$ map obtained by SEPG fitting with optimized $T_1$ is generally smaller. It is noteworthy to point out that since the data sets with 180° and 120° FAs were obtained by two separate acquisitions, there is slight difference between the two imaging slices due to inter-scan movement even though the same slice was prescribed.

Figure 10:
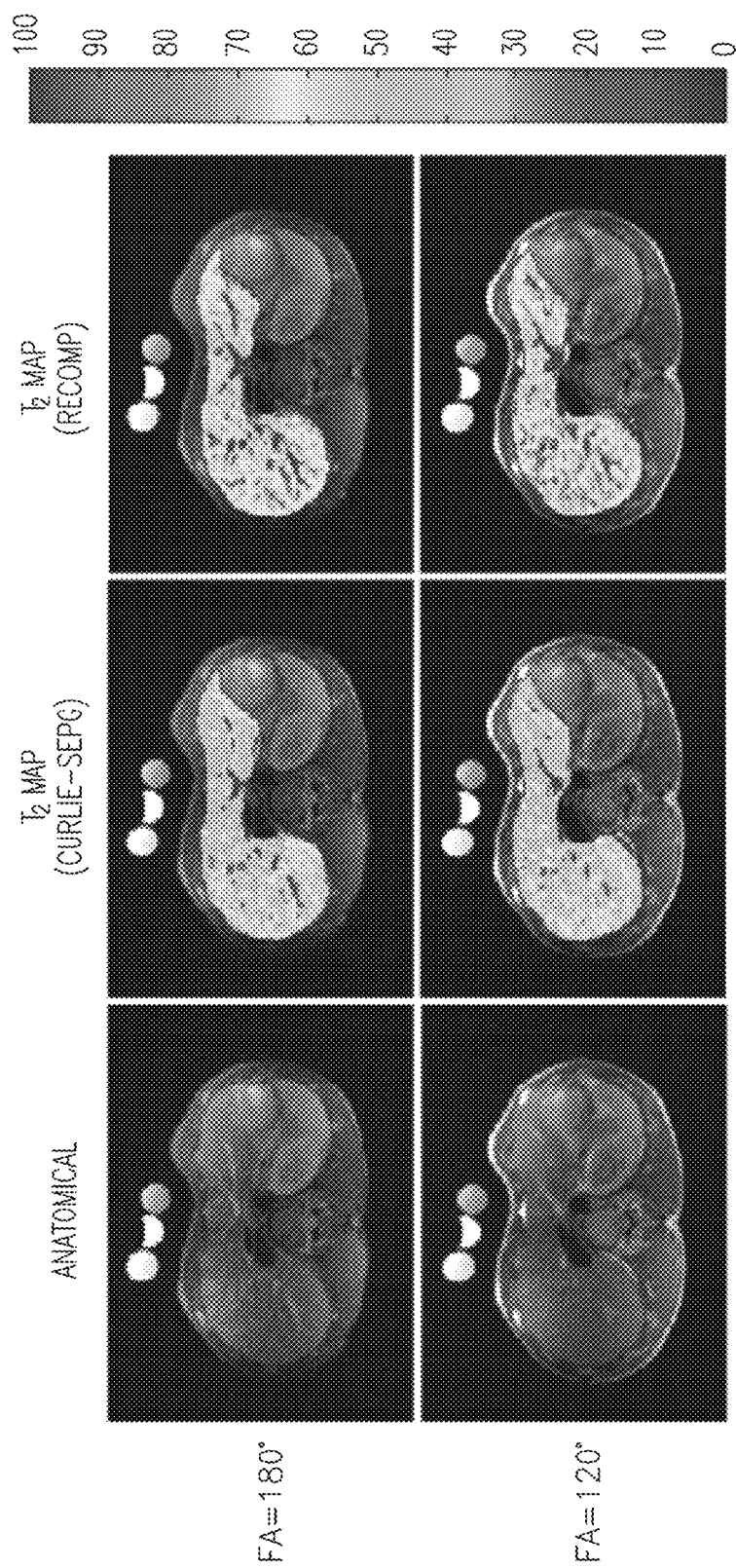
FIG. 10 is a series of abdominal images with a $T_2$ map overlay onto an anatomical image with the $T_2$ maps being generated by REPCOM as well as the techniques described herein.

An investigation of the utility of $T_2$ mapping with CURLIE and SEPG fitting was conducted for abdominal imaging where high undersampling is needed due to the acquisition time constraint imposed by the breath hold. FIG. 10 shows the anatomical images and the voxel-wise $T_2$ maps of an abdominal slice. The maps were reconstructed from highly undersampled data (16 radial k-space lines per TE; 4.0% sampled with respect to the Nyquist criteria) by REPCOM and CURLIE with optimized $T_1$ SEPG fitting. Three phantoms with known $T_2$ values were placed above the subject during data acquisition and used as the gold standard (due to the breath hold limitation, it was not possible to obtain a gold standard data set for the liver $T_2$ map). The CURLIE reconstructions were performed with $L=6$. The PCs were obtained from training curves generated for a $T_2$ range of 35-350 ms, $T_1=+\infty$ and $B_1=0.5$-$1.2$. As shown in the figure, the $T_2$ estimates obtained from the REPCOM reconstruction increase when the FA decreases from 180° to 120°, while the $T_2$ maps reconstructed by CURLIE with SEPG fitting (optimized $T_1=500$ ms) are comparable for the two different FAs. Note that since the data sets with 180° and 120° FAs were obtained from two separate breath hold acquisitions the slices are similar but not exactly the same.

The $T_2$ estimates of the phantoms imaged with the liver subject are summarized in Table 3, illustrated in FIG. 11. For both 180° and 120° prescribed FAs, the $T_2$ estimates by CURLIE with SEPG fitting have <3.5% error compared to the gold standard $T_2$. When the effect of indirect echoes is not taken into account in the reconstruction (as in REPCOM), the error can be up to 14% and 38% for FAs of 180° and 120°, respectively. The trend is similar as that shown in FIG. 10, and the fact that the $T_2$ values obtained from CURLIE with SEPG fitting are very similar to the gold standard $T_2$ values indicates that the CURLIE $T_2$ maps shown in FIG. 10 are accurate.

Figure 12:
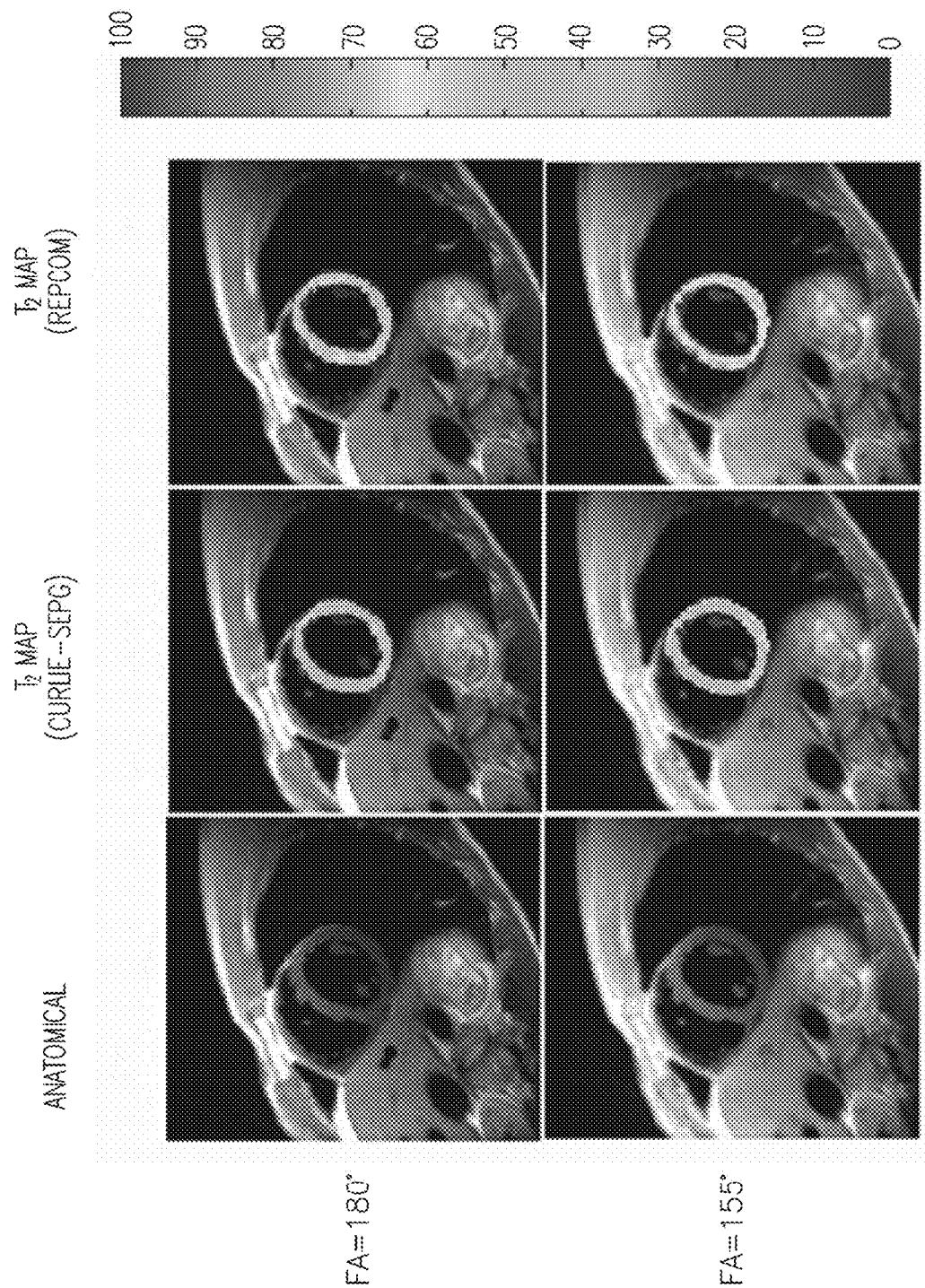
FIG. 12 is a series of cardiac images with anatomical images and an overlay of the $T_2$ map using the present techniques and REPCOM.

CURLIE with optimized $T_1$ SEPG fitting can also be applied for $T_2$ mapping of the myocardium using data acquired in a single breath hold. In cardiac imaging it is desirable to keep the echo train as short as possible to avoid cardiac motion during data acquisition thus, a short refocusing pulse (i.e., FA<180°) is typically used. FIG. 12 shows the anatomical short-axis cut of the heart acquired with a double-inversion radFSE sequence and $T_2$ maps reconstructed via CURLIE with SEPG fitting (optimized $T_1=700$ ms) and REPCOM. The maps were reconstructed from 16 radial k-space lines per TE (4.0% sampled). Similar to the observation made for the liver, the $T_2$ maps reconstructed by CURLIE with SEPG fitting are comparable for the two different refocusing pulses, whereas the $T_2$ maps reconstructed by REPCOM show a greater disagreement between the two refocusing pulses.

Discussion

The CURLIE process has been shown to accurately reconstruct the decay curves with indirect echoes from highly undersampled radial MESE data, CURLIE uses a linear approximation of the signal decay allowing for the incorporation of the highly non-linear SEPG model to account for the effects of indirect echoes. Moreover, the TE images generated via CURLIE have high spatial and temporal resolution. As a result, CURLIE combined with SEPG fitting enables accurate $T_2$ estimation from highly undersampled radial MESE data allowing for the reconstruction of $T_2$ maps from data acquired in a short period of time. For instance $T_2$ maps of the whole brain can be achieved in 4 min or less (depending on the degree of undersampling used). Maps of the thoracic cavity and abdomen can be obtained in a breath hold.

As shown in this work, the indirect echoes which are inherent to MESE acquisitions cause a significant (positive)

$T_2$ bias if data are reconstructed assuming an exponential decay. The indirect echo effect is more pronounced for longer $T_2$s and as the FA of the refocusing pulses deviate from the ideal 180° (17). Thus, without indirect echo compensation, the $T_2$ estimates from MESE data will depend on the profile of the radio frequency pulse, $B_1$ imperfections, as well as the TE coverage used in the experiment (number of TE points and echo spacing). As a result, the inter-site or inter-scan reproducibility of $T_2$ measurements can be greatly impacted. Indirect echoes also limit the use of MESE for $T_2$ mapping at higher fields (field strength≥3T) where SAR limits the use of 180° refocusing pulses or in cardiac applications where shorter refocusing pulses are used to reduce the acquisition window and minimize the effects of motion.

Our results showed that when curves are reconstructed with CURLIE followed by SEPG fitting the $T_2$ bias of phantoms (compared to a gold standard) are small and not dependent on the $T_2$ values and FAs of the refocusing pulses even for data acquired with a high degree of undersampling. The same trend in seen vivo: the $T_2$ maps of brain, liver and heart reconstructed from highly undersampled data with CURLIE and SEPG fitting are not affected by the prescribed FA of the refocusing pulses as those reconstructed from the REPCOM algorithm. Overall, the technique should provide a fast method for $T_2$ mapping that is less dependent on the experimental conditions including the magnetic fields strength. These unique characteristics should make the technique practical for clinical use.

In this work SEPG fitting was performed for $T_1=\infty$ or an optimized $T_1$, however, in the reconstruction of the decay curves via CURLIE, $T_1$ was fixed to infinity. This can be optimized using prior information of the object being imaged and the scanner and imaging parameters. Similar optimization can be performed for the $T_2$ and $B_1$ for the generation of the PCs. The $T_2$ range used to generate the training curves can also be optimized by using prior knowledge based on the anatomy being imaged, or estimated by prior $T_2$ mapping using a different algorithm (e.g. REPCOM or the echo sharing algorithm described in Ref. 14). In this work we used 6 principal components to approximate the signal model and showed that the $T_2$ can be accurately estimated in phantoms and a series of in vivo applications such as brain, myocardium and liver. In this work, the number of principal components ($L$) was determined empirically for the given training set. It is expected that smaller $L$ could yield similar results for an optimized training set. However, given the ranges and/or distributions of $T_2$, $T_1$ and $B_1$, the optimal $L$ and design of the training curves remain open problems.

Although SEPG fitting yields fitted $B_1$ maps in addition to the $T_2$ maps, the fitted $B_1$ maps estimated from our algorithm showed $T_1$ effects. These manifested as fluctuations along interfaces between tissues with very different $T_1$s (e.g., gray-white matter tissue and CSF or liver parenchyma and blood vessels). However, the nature of the $B_1$ maps did not affect the $T_2$ results. We verified this experimentally by comparing the $T_2$ maps obtained from the CURLIE-SEPG method to those resulting from just SEPG fitting (using standard sampled data when available) or by a using smoothing constraint for the $B_1$ maps before $T_2$ estimation. The $T_2$ maps were similar regardless of the $B_1$ maps.

For the non-optimized Matlab code used here, the reconstruction took about 40 min using a single core of a desktop computer (Intel Core 2 Quad CPU, 2.4 GHz) for a single slice when the data were acquired with eight coils, 256 k-space lines. However, a significant reduction in reconstruction time is expected when the reconstruction code is optimized and parallelized since most of the computation time was spent on matrix multiplication.

Joint Bi-Exponential Fitting Processing

In another aspect, the linearization approach can be used to estimate $T_2$ from highly undersampled data that obeys a signal model where multiple tissue components or chemical species are contained in a voxel. In these cases the measurements obtained are a linear combination from more than one component (with different weightings) and noise. Thus, the linearization process can deal better with signal models based on multiple components. For example, if PCs are used as a linearization tool, a multiple component system can be represented by a linear combination of the PCs. However, a problem encountered with fitting algorithms that handle multi-component data is that the parameter estimation is significantly more affected by the level of noise in the measurement data compared to single component systems. For a multiple component model the techniques described herein utilize linear combination weighting variation to improve accuracy of estimation by fitting the data jointly (i.e., joint bi-exponential fitting processing or JBF). One application of the joint approach is to correct for the effects of partial volume in quantitative magnetic resonance imaging acquired from highly undersampled data.

For the parameter estimation involving multi-component systems conventional approaches increase the amount of measurements in order to increase the number of points needed to fit the data and/or increase the signal to noise ratio of each data point. As discussed above, these approaches typically require long acquisition times which in many cases (such as in clinical MRI) is not a viable option. As an alternative to increasing the amount of measurements, others have proposed to average information within a region-of-interest (ROI); this is referred to as the region fitting (RF) algorithm. The RF algorithm does not take into account the natural variations occurring within the ROI. For example, in the case of parameter estimation for small liver lesions, there is variation in the lesion fraction (relative amount of lesion and liver tissues) within a given imaging voxel. This natural variation is ignored in the conventional RF approach. The joint fitting approach described herein utilizes data representative of this variation to improve parameter estimation.

As will be described in greater detail below, the JBF processing provides fast and accurate parameter estimation in the presence of partial volume from MRI data acquired in a short period of time. The commercial impact could be considerable given that the concept could be applied across vendor platforms and across an array of acquisition techniques as well as disease types. Specific technique application for liver lesion imaging is provided in this disclosure. Liver imaging is one of the largest growing applications for clinical MRI and the JBF processing could have significance for applications including tumor characterization. Those skilled in the art will appreciate that the JBF techniques described herein can be applied to other tissue types beside the examples of liver tissue described herein.

As previously discussed, MRI techniques have a significant limitation of acquisition time. For example, experimental data is shown where the JBF processing combined with a radial MRI technique is used to yield images with high spatial and temporal resolution from which accurate $T_2$ maps of tissues are obtained in the presence of partial volume effects. Normally this is not feasible with conventional techniques within important tissues of interest, such as the liver, where data needs to be acquired in a short period of time (e.g., breath hold) to mitigate the effects of motion, as related to breathing. The techniques described herein allow the imaging data to be obtained within a breath hold period. While the data collected within a breath hold is highly undersampled, the JBF processing can still generate images with quality that matches image quality of longer data acquisition times. Currently, no other techniques are available to achieve this degree of acceleration when high temporal and spatial resolution is required for tissue characterization.

Parameter estimation is widely used in many fields. In many situations, the measurements obtained are a linear combination from more than one component (with different weightings) and noise. For parameter estimation from multicomponent data in the presence of noise we propose a novel technique which uses a joint bi-exponential fitting (JBF) approach. The new algorithm yields accurate estimates with significantly less data compared to conventional fitting methods.

The JBF algorithm is described here in the context of $T_2$ estimation for small structures (e.g., tumors or lesions) embedded in a background (e.g., tissue parenchyma such as liver, brain, or muscle). However, the methodology can be extended to other applications in the field of medical imaging or imaging technology in general.

$T_2$ Estimation for Small Tumors Embedded in a Background Tissue

The characterization of small lesions embedded in a tissue background can be challenging due to the contamination from the background. This is known as the partial volume effect or PVE and is the main source of error in small lesion classification based on techniques such as $T_2$-weighted, diffusion-weighted MRI, and contrast enhancement techniques (32-34).

If we consider a lesion with a diameter <15 mm and a 6-8-mm thick imaging slice, most of the voxels within the ROI containing the lesion are contaminated with signal from the background tissue. Thus, any parameter estimated for the lesion will be affected by the PVE. In the case of $T_2$ estimation, the PVE can be accounted for by using the following multi-exponential signal model:

$$s(t) = I_l e^{-t/T_{2l}} + I_b e^{-t/T_{2b}} + \varepsilon(t), \quad [10]$$

where $I_l$, $I_b$ are the initial signal intensities of the lesion and the background tissue (i.e., signal at time t=0 ms), $T_{2l}$, $T_{2b}$ are the corresponding $T_2$ values, and $\varepsilon(t)$ is the noise of the given voxel at time t. Given the signals of a voxel at N TE time points, least-square fitting can be used to estimate the parameters $I_l$, $I_b$, $T_{2l}$, $T_{2b}$ in a voxel-wise fashion:

$$\hat{I}_l, \hat{I}_b, \hat{T}_{2l}, \hat{T}_{2b} = \underset{I_l, I_b, T_{2l}, T_{2b}}{\mathrm{argmin}} \left\{ \sum_{n=1}^{N} \|I_l e^{-TE_n/T_{2l}} + I_b e^{-TE_n/T_{2b}} - s(TE_n)\|^2 \right\}. \quad [11]$$

Due to the nature of the multi-exponential model and the presence of noise, the conventional voxel-wise bi-exponential fitting (VBF) algorithm leads to large uncertainty of the fitted parameters (35). One way to improve fitting for bi-exponential models is to reduce the noise. Thus, as an alternative to VBF, the RF approach was proposed (36). The algorithm is based on averaging the data from all the voxels within the ROI at each time point prior to fitting with Equation [11]. RF is more stable than VBF (35), however, the averaging procedure disregards the information on the lesion fraction $$LF = \frac{I_l}{I_l + I_b}$$

from each voxel.

The Joint Bi-Exponential Fitting (JBF) Algorithm (37):

For the case of small lesions, the LF may vary significantly from voxel to voxel and this variation can be utilized to improve fitting in a bi-exponential model. In order to utilize this variation we propose a $T_2$ estimation algorithm that estimates $T_{2l}$, $T_{2b}$ for all voxels jointly. The joint $T_2$ estimation relies on the assumption that for small lesions (diameter <15 mm) the $T_{2l}$, $T_{2b}$ for all voxels within the lesion's ROI can be considered homogenous which is a realistic assumption for small lesions.

Let $I_l^1, I_l^2, \ldots, I_b^1, I_b^2, \ldots, I_b^M$ be the initial signal intensities of lesion and background, respectively, for each of the M voxels within the lesion's ROI. Let $s^1(TE_n)$, $s^2(TE_n), \ldots, s^M(TE_n)$ be the signals from these M voxels at time $TE_n$. Under the assumption of homogeneity, we can constrain $T_{2l}^m$, $T_{2b}^m$ to two global values $\bar{T}_{2l}$ and $\bar{T}_{2b}$ within the lesion's ROI. The JBF process for $T_2$ estimation can be formulated as:

$$\hat{\bar{T}}_{2l}, \hat{\bar{T}}_{2b} = \mathrm{argmin}\left\{ \sum_{n=1}^{N} \sum_{m=1}^{M} \|I_l^m e^{-t_n/\bar{T}_{2l}} + I_b^m e^{-t_n/\bar{T}_{2b}} - s_m(TE_n)\|^2 \right\}. \quad [13]$$

Figure 13:
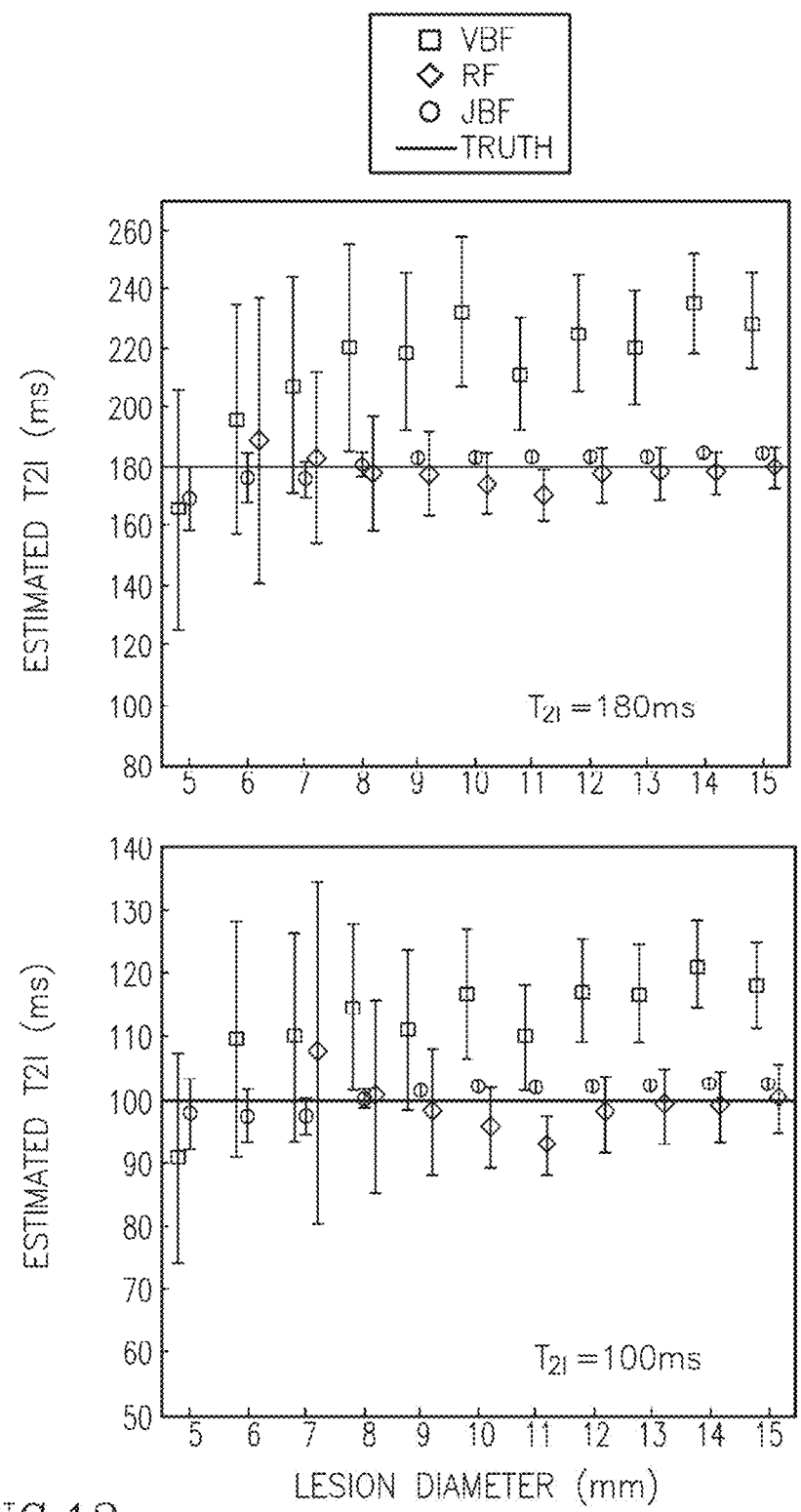
FIG. 13 is a table illustrating the bar plots of estimated data versus lesion diameter for various fitting algorithms.

JBF Versus the Conventional VBF and Region Fitting Algorithms:

Simulations were conducted to compare the VBF, region fitting and JBF algorithms for the specific task of estimating $T_{2l}$ for small lesions. FIG. 13 shows plots of the estimated $T_{2l}$ versus lesion diameter according to the VBF, RF, and JBF algorithms. Simulations are presented for mean $T_{2l}$ values of 180 ms and 100 ms with a mean $T_{2b}$ of 40 ms. These represent common values observed in focal liver lesions and liver parenchyma. In FIG. 13, the errors are plots of estimations by different algorithms versus the lesion diameter are shown. Data points that have out-of-range error bars are not shown.

As seen in the FIG. 13, the conventional VBF approach suffers from large biases; the bias in the estimated $T_{2l}$ can be up to ±35%. The RF approach suffers from large uncertainties. In fact, some of the error bars in FIG. 13 for the RF algorithm were well out of the range of the plots thus, the data are not shown. The proposed JBF algorithm has significantly smaller standard deviations and more accurate means compared to the other two algorithms, especially for lesions with diameters smaller than 10 mm.

Figure 14A:
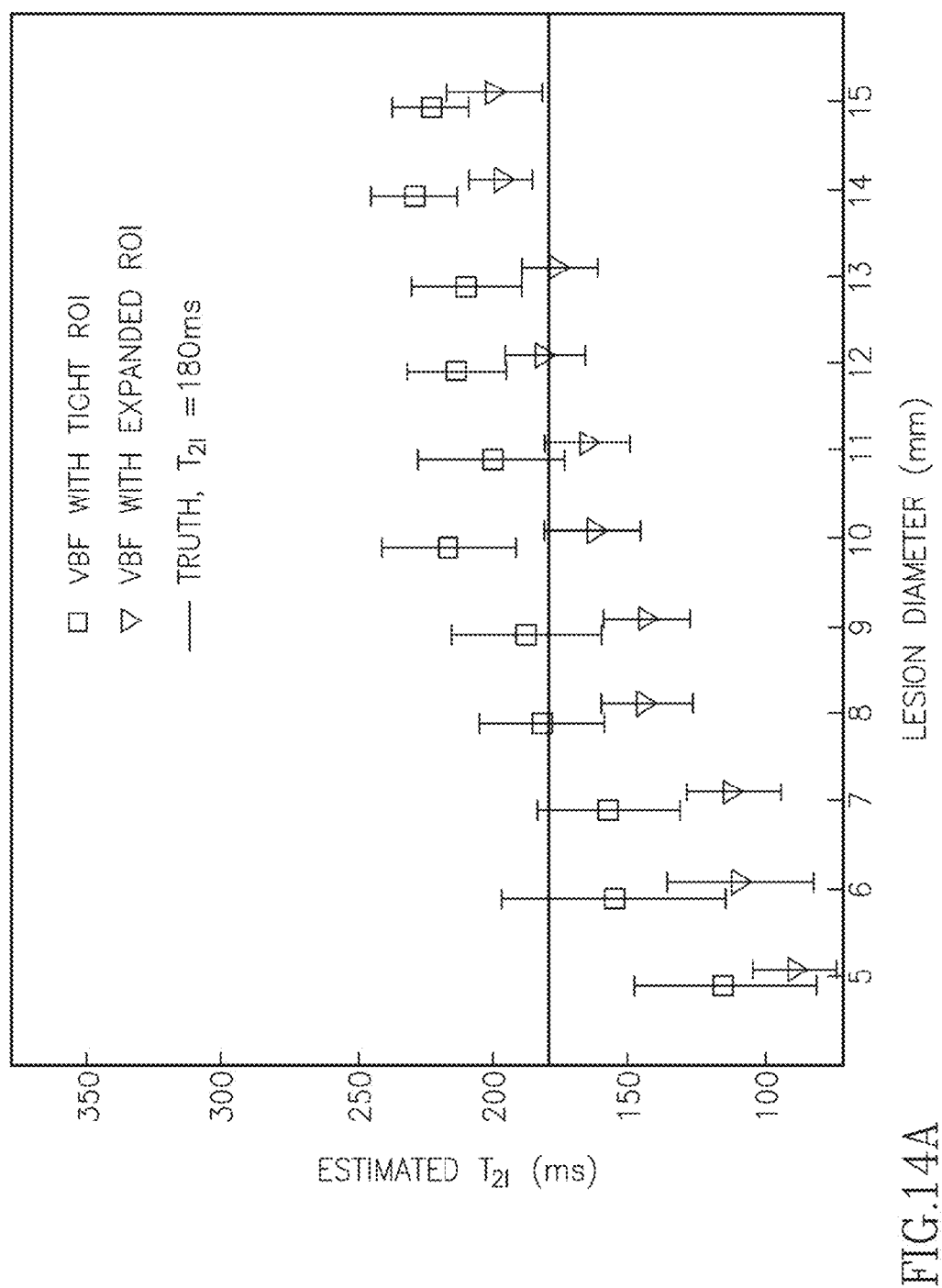
FIGS. 14A-14C are a series of graphs illustrating $T_2$ errors estimated by various fitting algorithms for a tight region of interest and an expanded region of interest.
Figure 14B:
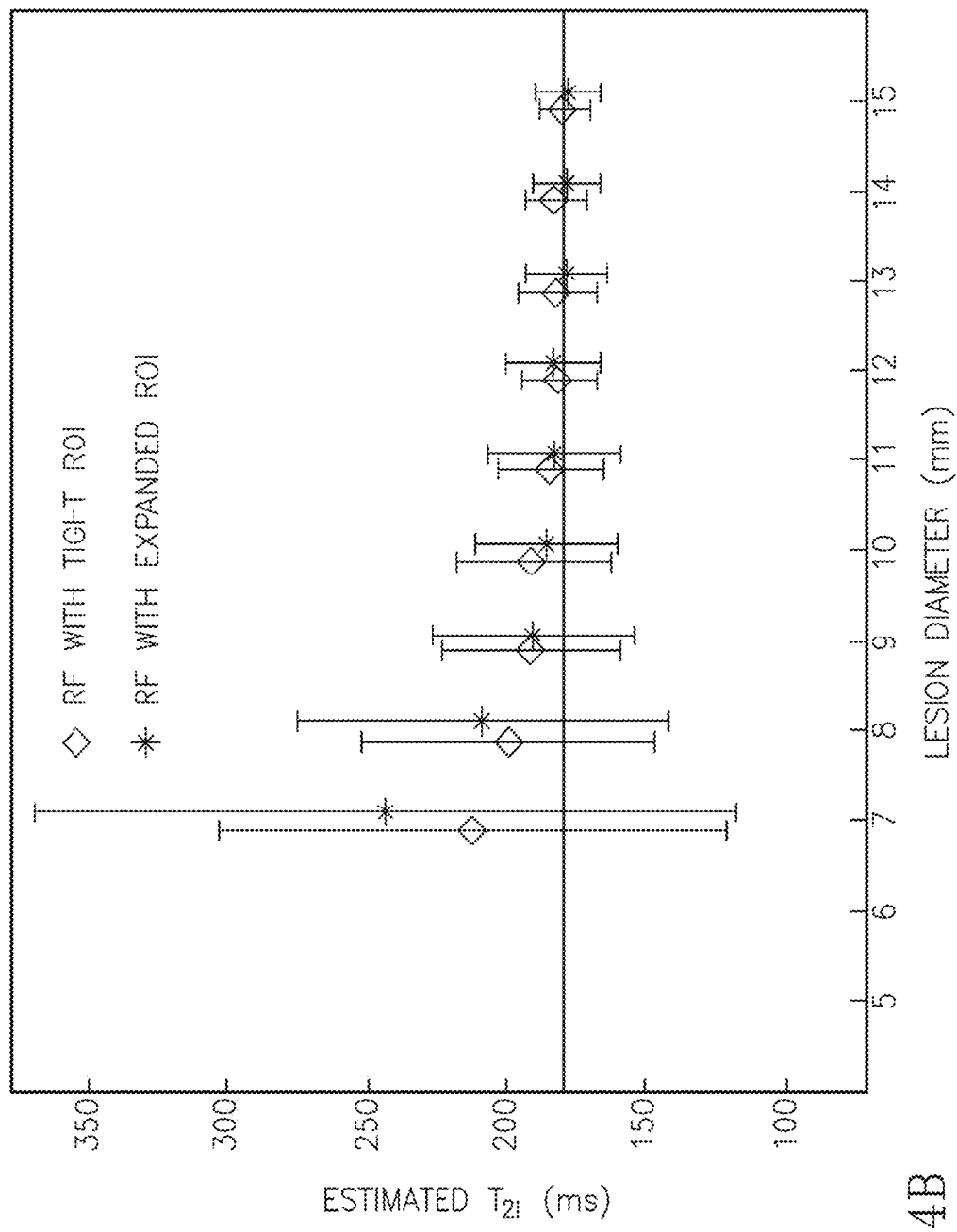
Figure 14C:
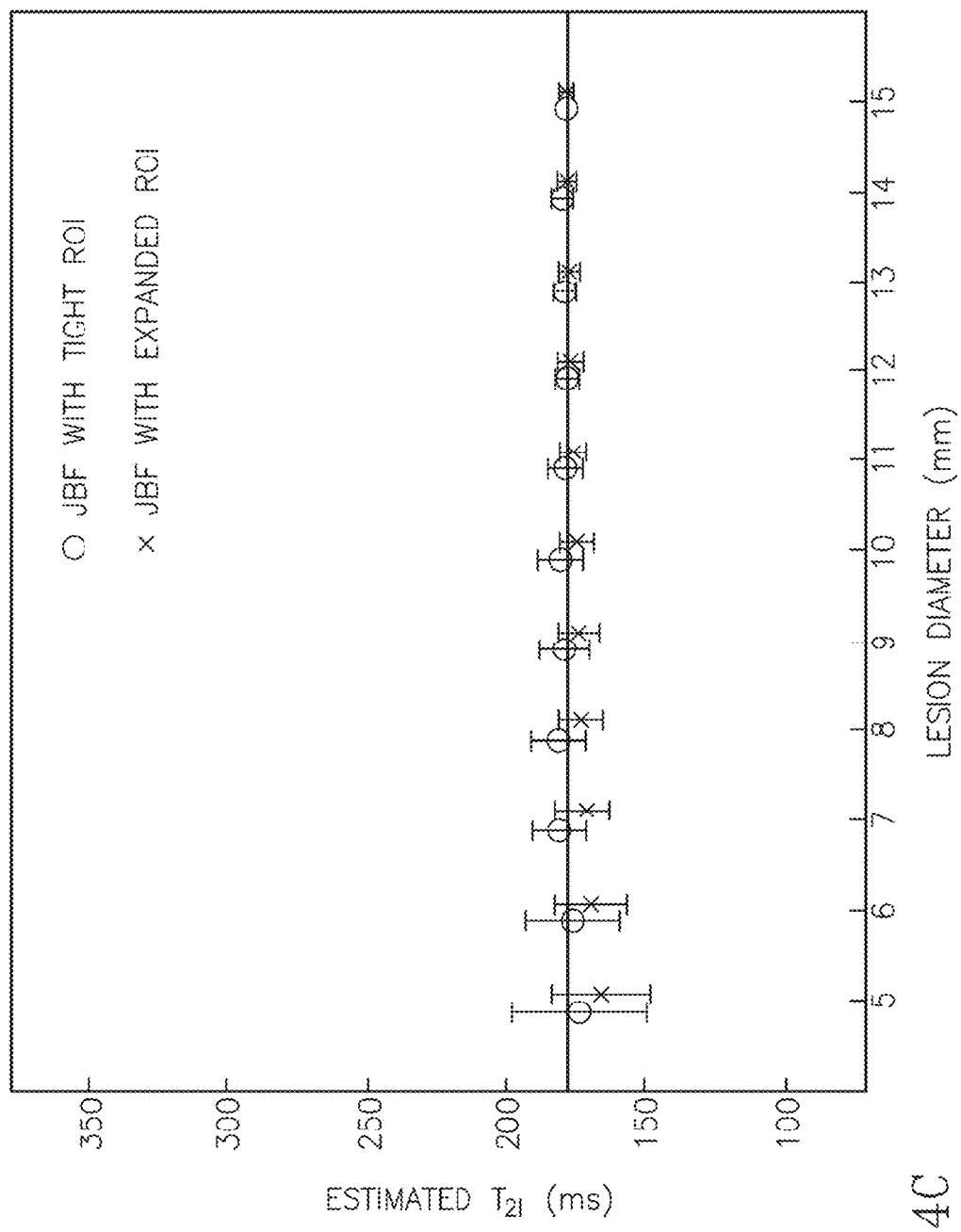

In FIG. 13 we used an ROI consisting of voxels containing the lesion (tight ROI). In practice, a tight ROI may not always be achievable, particularly for small lesions. Under the assumption that the voxels next to the lesion's ROI have similar $T_{2b}$ as the background voxels within the ROI, it should be possible to obtain accurate $T_{2l}$ estimates even if the ROI is not tight. To prove this concept an expanded ROI was generated by including all immediate neighboring voxels to the tight ROI. FIG. 14 shows the performances of the three algorithms for the tight and expanded ROIs. The VBF estimates varied greatly when the expanded ROI was used.

The error bars of RF have large overlap between the two ROIs, but the variations of the bias between the two ROIs for small diameters are large than that of JBF. For JBF the difference of the means obtained by the two ROIs is <5%. This demonstrates the insensitivity to ROI drawing of the JBF algorithm.

A study on a physical phantom was also conducted. A phantom composed of four glass tubes ending in a spherical bulb was used to represent small spherical lesions. The tubes were filled with Magnevist (Bayer HealthCare Pharmaceuticals Inc., Germany) solutions of different concentrations to yield different $T_{2l}$ values. The tubes were inserted in a background solution that corresponded to $T_{2b}$~40 ms.

The physical phantom results are summarized Table 4, shown in FIG. 15. Table 4 illustrates the results from the physical phantom showing the percent error in $T_2$ estimates and compares the % errors of the estimated $T_{2l}$ values obtained by the VBF, RF, and JBF algorithms with respect to the gold standard (obtained from a separate single-echo spin-echo experiment using samples with no background) for a tight and expanded ROI. The results show that VBF has the largest biases and the method is very sensitive to ROI drawing; the % error can vary up to almost 80% between a tight and an expanded ROI. RF has smaller biases than VBF and the method is less dependent on the ROI drawing; the variation caused by the two ROIs is under 35%. The proposed JBF algorithm is the most accurate (bias <3%) and the method is highly insensitive to ROI drawing; the largest observed variation for different ROIs is 1%.

Extension of JBF for Undersampled Radial FSE Data (38):

Because in clinical MRI the acquisition of data for parameter mapping needs to be within the time constraints of a clinical examination (in many cases a breath hold time), the amount of data available for parameter estimation is limited.

For the case of $T_2$ mapping the goal is to use the JBF approach with undersampled FSE data. In a breath hold experiment this means that we will have 1/16 of the data typically required for $T_2$ mapping. Thus, we propose combining JBF with a linearized-model-based reconstruction, recently developed by our group for $T_2$ mapping using undersampled radFSE data (12). We named the combined methodology PURIFY for Partial volUme coRrected rolbased $T_2$ Fitting of highly undersampled data.

We tested PURIFY using the physical phantom with Magnevist solutions to yield $T_{2l}$ of 69.0 ms and 179.8 ms and $T_{2b}$=40.1 ms. In the experiment we used undersampled radFSE data acquired in only 22 s. The $T_{2l}$ estimates obtained from JBF and single exponential fitting (i.e., no partial volume correction) are shown in Table 5, illustrated in FIG. 16. The data in Table 2 results from a physical phantom showing $T_2$ estimates for the JBF using highly undersampled data. Note that with single exponential fitting the $T_{2l}$ values are significantly lower than the gold standard due to contamination from background tissue. When JBF is used the $T_{2l}$ values are close to the gold standard. This proves the concept that $T_2$ mapping with partial volume correction using highly undersampled data is achievable with the JBF approach.

Figure 17:
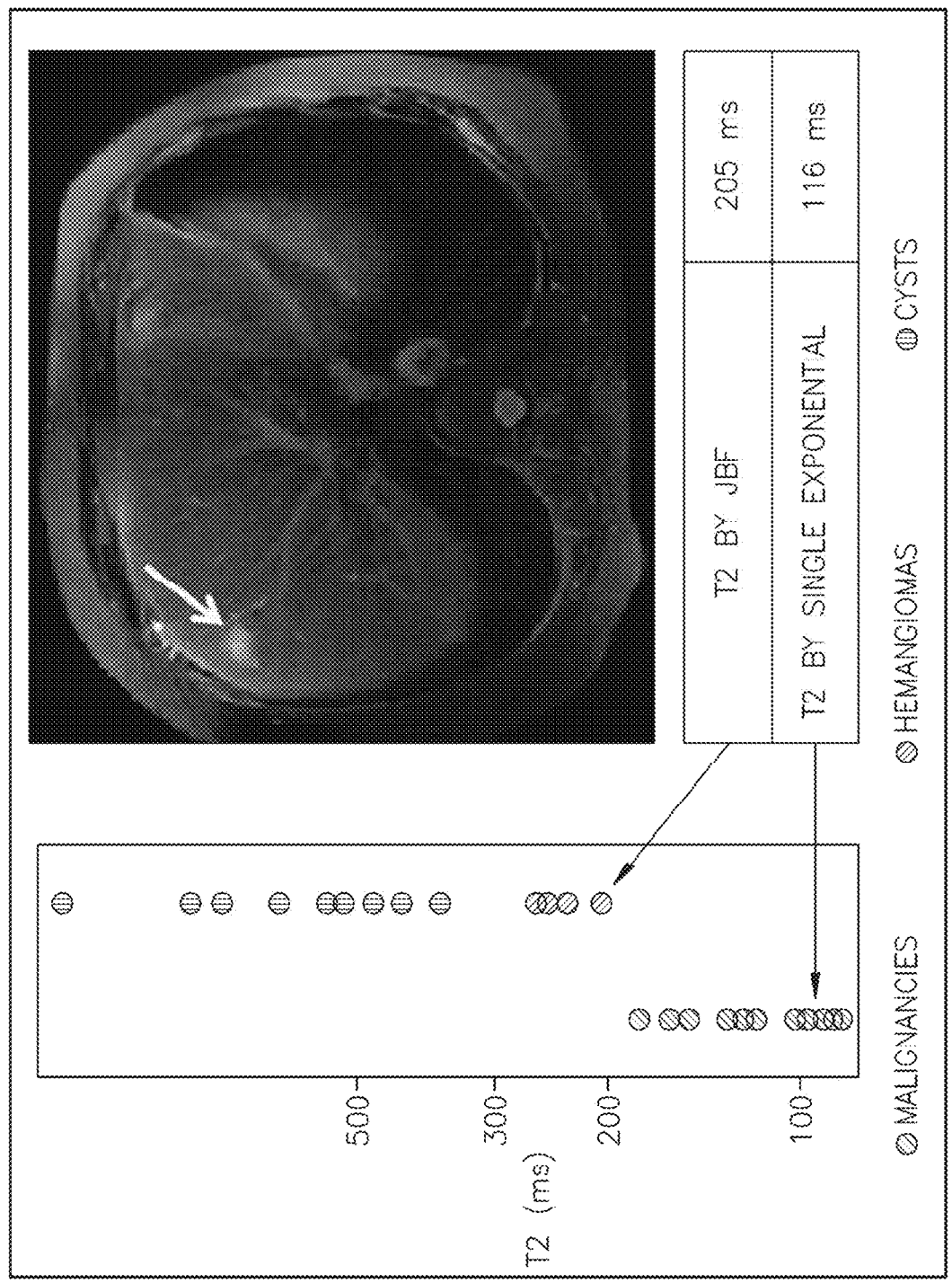
FIG. 17 is an image illustrating a lesion classification plot generated using data from a set of subjects with liver lesions where the $T_{2L}$ values were estimated by the fitting algorithm described herein and a single exponential fitting from highly undersampled data acquired in one breath hold.

PURIFY was also tested in vivo. FIG. 17 shows the image corresponding to an abdominal scan of a subject with a small hemangioma. The figure also shows a plot of lesion classification based on $T_2$ values generated from a set of 41 patients with larger liver lesions (>1.5 cm in diameter) (12, 24). Note that when a single exponential fit is used, the $T_2$ of the hemangioma falls within the range of malignant lesions (false positive) because the PVE due to liver contamination is not taken into account. When the JBF algorithm is used, the lesion is within the range of benign lesions (true negative). It is noteworthy to mention that the lesion classification was possible from data acquired in a breath hold (22 s).

CONCLUSIONS

In this work, it has been shown by numerical simulation, phantom and in vivo data that the proposed CURLIE algorithm can accurately reconstruct the decay curves with indirect echoes from highly undersampled radial MESE data. Accurate $T_2$ estimates can then be derived from the TE curves via SEPG fitting. The use of highly undersampled radial MESE data allows for the fast acquisition of data. The correction for indirect echoes reduces inaccuracies in $T_2$ mapping due to imperfect refocusing pulses making $T_2$ mapping with MESE accurate when the FA of the refocusing pulses are less than the ideal 180°; this is particularly important at higher magnetic fields as well as in certain cardiac applications. Overall, the CURLIE algorithm combined with SEPG fitting enables fast $T_2$ estimation which is less dependent on the experimental conditions used for data acquisition.

In another example of image processing using highly undersampled imaging data, the partial volume correction process of PURIFY provides very accurate results with a minimal amount of data. These improvements should make $T_2$ mapping more practical for clinical use.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. SEP In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Farraher S W, Jara H, Chang K J, Ozonoff A, Soto J A. Differentiation of hepatocellular carcinoma and hepatic metastasis from cysts and hemangiomas with calculated T2 relaxation times and the T1/T2 relaxation times ratio. Journal of Magnetic Resonance Imaging. 2006; 24(6): 1333-1341.
2. Cieszanowski A, Szeszkowski W, Golebiowski M, Bielecki D K, Grodzicki M, Pruszynski B. Discrimination of benign from malignant hepatic lesions based on their T2-relaxation times calculated from moderately T2-weighted turbo SE sequence. Eur. Radiol. 2002; 12:2273-2279.
3. Deng J, Larson A C. Modified PROPELLER Approach for T2-Mapping of the Abdomen, Magnetic Resonance in Medicine 2009; 61:1269-1278.
4. Kim D, Jensen J H, Wu E X, Sheth S S, Brittenham G M. Breathhold Multiecho Fast Spin-Echo Pulse Sequence for Accurate R2 Measurement in the Heart and Liver, Magnetic Resonance in Medicine 2009; 62:300-306.
5. Pell G S, Briellmann R S, Waites A B, Abbott D F, Lewis D P and Jackson G D. Optimized clinical T2 relaxometry with a standard CPMG sequence. Journal of Magnetic Resonance Imaging 2006, 23: 248-252.
6. Deoni S C L, Peters T M, Rutt B K. High-resolution T1 and T2 mapping of the brain in a clinically acceptable time with DESPOT1 and DESPOT2. Magnetic Resonance in Medicine. 2005; 53: 237-241.
7. Rugg-Gunn F J, Boulby P A, Symms M R, Barker G J, Duncan J S. Whole-brain T2 mapping demonstrates occult abnormalities in focal epilepsy. Neurology 2005; 64:318-325.
8. Kurki T, Lundbom N, Valtonen S. Tissue characterisation of intracranial tumours: the value of magnetisation transfer and conventional MRI. Neuroradiology 1995; 37:515-521.
9. Laakso M P, Partanen K, Soininen H, Lehtovirta M, Hallikainen M, Hänninen T, Helkala E-L, Vainio P, Riekkinen P J Sr. MR $T_2$ relaxometry in Alzheimer's disease and age-associated memory impairment. Neurobiol Aging 1996; 17:535-540.
10. Jacobs M A, Mitsias P, Soltanian-Zadeh H, Santhakumar S, Ghanei A, Hammond R, Peck D J, Chopp M, Patel S. Multiparametric MRI tissue characterization in clinical stroke with correlation to clinical outcome: part 2. Stroke 2001; 32:950-957.
11. Block K T, Uecker M, Frahm J. Model-Based Iterative Reconstruction for Radial Fast Spin-Echo MRI. IEEE Transactions on Medical Imaging, 2009 (28): 1759-1769.
12. Huang C, Graff C G, Clarkson E W, Bilgin A, and Altbach M I, T2 Mapping from Highly Undersampled Data by REconstruction of Principal COmponent coefficient Maps (REPCOM) using Compressed Sensing. Magnetic Resonance in Medicine 2012; 67(5):1355-1366.
13. Doneva M, Senegas J, Bornert P, Eggers H, Mertins A, Compressed Sensing Reconstruction for Magnetic Resonance Parameter Mapping, Magnetic Resonance in Medicine 2010; 64(4): 1114-1120.
14. Altbach M I, Bilgin A, Li Z, Clarkson E W, Trouard T P, Gmitro A F. Processing Of Radial Fast Spin-Echo Data For Obtaining T2 Estimates From A Single K-Space Data Set. Magnetic Resonance in Medicine 2005; 54(3): 549-559.
15. Samsonov A. A Novel Reconstruction Approach Using Model Consistency Condition for Accelerated Quantitative MRI (MOCCA). In Proceedings of the International Society for Magnetic Resonance in Medicine 2012; (20): 358.
16. Doneva M, Sénégas J, Börnert P, Eggers H, Mertins A. Accelerated MR Parameter Mapping Using Compressed Sensing With Model-Based Sparsifying Transform. In Proceedings of the International Society for Magnetic Resonance in Medicine 2009; (17): 2812.
17. Lebel R M and Wilman A H. Transverse Relaxometry with Stimulated Echo Compensation. Magnetic Resonance in Medicine 1020; 64: 1005-1014.
18. Poon C S, Henkelman R M. Practical T2 quantitation for clinical applications. Journal of Magnetic Resonance Imaging 1992; 2:541-553.
19. Majumdar S, Orphanoudakis S C, Gmitro A, O'Donnell M, Gore J C. Errors in the measurements of T2 using multiple-echo MRI techniques. I. Effects of radiofrequency pulse imperfections. Magnetic Resonance in Medicine 1986; 3:397-417.
20. Does M D, Snyder R E. Multiecho imaging with suboptimal spoiler gradients. Journal of Magnetic Resonance Imaging 1998; 131:25-31.
21. Hennig J. Multiecho Imaging Sequences with Low Refocusing Flip Angles. Journal of Magnetic Resonance 1988; 78: 397-407.
22. Huang C, Bilgin A, Graff C, Altbach M I, T2 Estimation For Small Lesions Using A Model-Based Reconstruction With Sparsifying Penalty Functions And Highly Undersampled Radial FSE Data. In Proceedings of the International Society for Magnetic Resonance in Medicine 2009; (17): 2740.
23. Sénégas J, Neu N, and Keupp J. Transverse Relaxometry with non-180° Refocusing Pulses. In Proceedings of the International Society for Magnetic Resonance in Medicine 2011; (19): 2761.
24. Altbach M I, Outwater E K, Trouard T P, Krupinski, Elizabeth A, Theilmann R J, Stopeck A T, Kono M, Gmitro A F. Radial fast spin-echo method for T2-weighted imaging and T2 mapping of the liver. Journal of magnetic resonance imaging: Journal of Magnetic Resonance Imaging 2002; 16(2):179-189.
25. Theilmann R J, Gmitro A F, Altbach M I, Trouard T P. View-ordering in radial fast spin-echo imaging. Magnetic Resonance in Medicine 2004; 51(4):768-774.
26. Haacke E M, Brown R W, Thompson M R, Venkatesan R, Magnetic Resonance Imaging: Physical Principles and Sequence Design, Chapter 16, Wiley, 1999. ISBN: 0-471-35128-8.

27. Simonetti O P, Finn J P, White R D, Laub G, Henry D A. Black blood T2-weighted inversion recovery MR imaging of the heart. Radiology 1996; (199): 49-57,
28. Polak E, Ribiere G. Note sur la Convergence des Méthodes de Directions Conjuguées, Revue Francaise d'Informatique et de Recherche Opérationelle 1969; 16: 35-43.
29. Deoni S C, Rutt B K, Peters R M, Rapid Combined T1 and T2 Mapping Using Gradient Recalled Acquisition in the Steady State. Magnetic Resonance in Medicine 2003; 49:515-526.
30. Wood M L, Bronskill M J, Mulkern R V, Santyr G E. Physical MR desktop data. Journal of Magnetic Resonance Imaging 1993; 3 Suppl.
31. Ratner A V, Okada R D, Newell J B, Pohost G M. The relationship between proton nuclear magnetic resonance relaxation parameters and myocardial perfusion with acute coronary arterial occlusion and reperfusion. Circulation. 1985; 71: 823-828,
32. Bruegel M, Rummeny E J, Hepatic metastases: use of diffusion-weighted echo-planar imaging, Abdom Imaging (2010) 35:454-461.
33. Parikh T, Drew S J, Lee V S, Won S, Hecht E W, Babb J S, Taouli B, Focal Liver Lesion Detection and Characterization with Diffusion-weighted MR Imaging: Comparison with Standard Breath-hold T2-weighted Imaging, Radiology, 2008, 246, 812-822.
34. Holzapfel K, Bruegel M, Gaa J, et al. Characterization of small (≤10 mm) focal liver lesions: Value of respiratory-triggered echo-planar diffusion-weighted MR imaging. European Journal of Radiology 2010; 76: 89-95.
35. Bretthorst G L. How accurately can parameters from exponential models be estimated? A Bayesian view. Concepts in Magnetic Resonance, 2005; A 27A(2): 73-83.
36. Bjarnason T A, McCreary C R, Dunn J F, Mitchell J R. Quantitative T2 Analysis: The Effects of Noise, Regularization, and Multivoxel Approaches. Magnetic Resonance in Medicine, 2010. 63:212-217.
37. Huang C, Graff C G, Clarkson E W, Bilgin A, and Altbach M I, "Region Based Joint Bi-exponential T2 Fitting for Small Lesions", Proceedings of the International Society for Magnetic Resonance in Medicine 2011; 18, 3247.
38. Huang C, Galons J P, and Altbach M I, Characterization of Small Liver Lesions using Partial Volume Corrected T2 Estimates Obtained from Highly Undersampled Radial Fast Spin Echo Data via PURIFY, submitted to the ISMRM Meeting, Sidney, Australia.
39. Altbach M I, "A radial magnetic resonance imaging method for imaging abdominal neoplasms', Methods of Cancer Diagnosis, Therapy, and Prognosis" Volume 3, 2009 edited by M. A. Hayat and published by Springer.

The invention claimed is:

1. A system comprising:
a magnetic resonance imaging (MRI) device configured to generate imaging data, the generated image data being generated using predetermined pulse sequence and being highly undersampled;
an interface configured to receive the imaging data generated by the MRI device; and
a processor configured to process the received imaging data using a linear approximation to a signal model characterizing a $T_2$ decay to thereby generate a corrected $T_2$ estimation map to compensate for errors in the highly undersampled generated imaging data caused by imperfections in the radio frequency refocusing pulses associated with the MRI device or multiple components due to the presence of different tissue species within a voxel to thereby generate and display a more accurate MRI image.

2. The system of claim 1 wherein the generated imaging data is radial fast-spin-echo acquisition data.

3. The system of claim 1 wherein the processor is configured to process the received imaging data to compensate for indirect echoes in the generated image data.

4. The system of claim 1 wherein the processor is configured to process the received imaging data to generate an estimation of the $T_2$ relaxation time.

5. The system of claim 1 wherein the processor is configured to process the received imaging data to apply a linearization model to the received image data and to compensate for indirect echoes in the generated image data.

6. The system of claim 1, further comprising:
a set of training curves generated for a range of expected $T_2$ values; and
a set of coefficients derived from a linear approximation model and the set of training curves, the coefficients being representative of $T_2$ decay curves in the presence of indirect echoes,
wherein the processor is further configured to apply the set of coefficients to the imaging data to compensate for imperfections in the refocusing pulses in the MRI device that distort the generated imaging data to thereby generate the $T_2$ map.

7. The system of claim 6 wherein the coefficients are derived from a group comprising principal components, a manifold, and a dictionary.

8. The system of claim 1 wherein the processor is configured to process the received imaging data from an imaging sample containing more than one tissue or chemical component within a voxel.

9. The system of claim 8 wherein the processor is configured to process the received imaging data using a set of initial lesion intensity values and a set of initial background intensity values for each voxel in a designated region of interest (ROI) containing an image of a lesion and to analyze the sets of initial intensity values in a fitting process to thereby generate the $T_2$ map representative of the lesion.

10. The system of claim 9 wherein the processor is configured to analyze the sets of initial intensity values using a joint bi-exponential fitting algorithm.

11. A method for processing imaging data generated by a magnetic resonance imaging (MRI) data comprising:
receiving the imaging data, the imaging data being generated using a predetermined pulse sequence and being highly undersampled; and
processing the received imaging data using a linear approximation to the signal model to thereby generate a corrected $T_2$ estimation map to compensate for errors in the highly undersampled generated imaging data caused by indirect echoes generated by imperfections in the radio frequency refocusing pulses associated with the MRI device or multiple components due to the presence of different tissue species within a voxel to thereby generate and display a more accurate MRI image.

12. The method of claim 11 wherein processing the received imaging data comprises generating a $T_2$ estimation map to thereby compensate for indirect echoes in the imaging data.

13. The method of claim 11 wherein processing the received imaging data comprises generating an estimation of the $T_2$ relaxation time.

14. The method of claim 11 wherein processing the received imaging data comprises applying a linearization model to the received imaging data and compensating for indirect echoes in the generated image data.

15. The method of claim 11, further comprising:
generating a set of training curves for a range of expected $T_2$ values;
deriving a set of coefficients from a linear model and the set of training curves, the principal components being representative of $T_2$ decay curves in the presence of indirect echoes; and
applying the set of coefficients to the imaging data to compensate for refocusing pulses in the MRI device that distort the generated imaging data to thereby generate the $T_2$ map.

16. The method of claim 15 wherein the coefficients are derived from a group comprising principal components, a manifold, and a dictionary.

17. The method of claim 11 wherein processing the received imaging data comprises processing the received imaging data from an imaging sample containing more than one tissue or chemical component within a voxel.

18. The method of claim 17 wherein processing the received imaging data uses a set of initial lesion intensity values and a set of initial background intensity values for each voxel in a designated region of interest (ROI) containing an image of a lesion and analyzing the sets of initial intensity values in a fitting process to thereby generate the $T_2$ map representative of the lesion.

19. The method of claim 18 wherein analyzing the sets of initial intensity values uses a joint bi-exponential fitting algorithm.

20. A system for processing magnetic resonance imaging data from an MRI device, comprising:
an interface configured to receive the imaging data generated by the MRI device, the imaging data being generated using a predetermined pulse sequence and being highly undersampled;
a set of training curves generated from imaging data for a range of expected $T_2$ values;
a set of principal components derived from the set of training curves, the principal components being representative of $T_2$ decay curves in the presence of indirect echoes generated by imperfections in the radio frequency refocusing pulses associated with the MRI device; and
a processor configured to apply the set of principal components to the imaging data to compensate for the imperfections in the refocusing pulses used in the MRI device that distort the generated imaging data to thereby generate a corrected $T_2$ map that reduces $T_2$ value dependence on the imperfection in the MRI device and to display a more accurate MRI image.

* * * * *